United States Patent
Pope et al.

(10) Patent No.: US 6,683,446 B1
(45) Date of Patent: Jan. 27, 2004

(54) ELECTRODE ARRAY FOR DEVELOPMENT AND TESTING OF MATERIALS

(76) Inventors: John Pope, 1166 N. 11th St., Laramie, WY (US) 82070; Daniel Buttry, 1305 E. Cutler, Laramie, WY (US) 82070

(*) Notice: Subject to any disclaimer, the term of this patent is extended or adjusted under 35 U.S.C. 154(b) by 0 days.

(21) Appl. No.: 09/869,102
(22) PCT Filed: Dec. 21, 1999
(86) PCT No.: PCT/US99/30812
§ 371 (c)(1), (2), (4) Date: Jun. 22, 2001
(87) PCT Pub. No.: WO00/37718
PCT Pub. Date: Jun. 29, 2000

Related U.S. Application Data

(60) Provisional application No. 60/118,067, filed on Feb. 1, 1999, and provisional application No. 60/113,162, filed on Dec. 22, 1998.

(51) Int. Cl.$^7$ .................. G01N 27/00; G01N 27/42; C25D 5/00
(52) U.S. Cl. .................. 324/71.1; 324/425; 205/81; 205/83
(58) Field of Search ................. 324/71.1, 425, 324/600, 444, 447; 205/81, 118, 687, 704, 82, 83; 73/866; 148/518

(56) References Cited

U.S. PATENT DOCUMENTS

| | | | | |
|---|---|---|---|---|
| 3,132,080 A | * | 5/1964 | Cann | 205/81 |
| 4,443,301 A | * | 4/1984 | Kerby | 324/71.1 |
| 4,465,565 A | * | 8/1984 | Zanio | 438/95 |
| 5,296,125 A | | 3/1994 | Glass et al. | 430/311 |
| 5,424,186 A | | 6/1995 | Fodor et al. | 435/6 |
| 5,456,819 A | * | 10/1995 | Lashmore et al. | 205/212 |
| 5,667,667 A | * | 9/1997 | Southern | 205/687 |
| 5,985,356 A | * | 11/1999 | Schultz et al. | 427/18 |
| 6,187,164 B1 | * | 2/2001 | Warren et al. | 205/81 |
| 6,203,758 B1 | * | 3/2001 | Marks et al. | 422/68.1 |
| 6,468,806 B1 | * | 10/2002 | McFarland et al. | 436/518 |

FOREIGN PATENT DOCUMENTS

| | | |
|---|---|---|
| WO | 98/03521 | 1/1998 |
| WO | 98/14641 | 4/1998 |

OTHER PUBLICATIONS

Shu Kobayashi, et al., "A New Methodology for Combinatorial Synthesis Preparation of Diverse Quinoline Derivatives Using a Novel Polymer–Supported Scandium Catalyst" American Chemical Society, vol. 118, pp. 8977–8978, 1996.

Gabriel Briceno, et al., "A Class of Cobalt Oxide Magnetoresistance Materials Discovered with Combinatorial Synthesis" Science, vol. 270, Oct. 13, 1995, pp. 273–275.

Scott E. Osborne, et al., "Nucleic Acid Selection and the Challenge of Combinatorial Chemistry" Chemical Review, vol. 97, No. 2, Mar./Apr. 1997.

Erik Reddington, et al., "Combinatorial Electrochemistry: A Highly Parallel, Optical Screening Method for Discovery of Better Electrocatalysts" Science, vol. 280, Jun. 12, 1998.

* cited by examiner

*Primary Examiner*—Anjan K. Deb
(74) *Attorney, Agent, or Firm*—Crowell & Moring LLP

(57) ABSTRACT

Methods and apparatus employ the use of arrays of two or more electronically discrete electrodes to facilitate high-throughput preparation and testing of materials with two or more elements. High rates of deposition, synthesis and/or analysis of materials are achieved with the use of arrays of electrodes whereby desired materials are developed. The high rate synthesis and/or analysis of an array of materials uses deposition control techniques in conjunction with the electrode array to develop a meaningful array of materials and to analyze the materials for desired characteristics to develop one or more materials with desired characteristics. The use of an array of electrodes enables high throughput development of materials having scientific and economic advantages.

28 Claims, 11 Drawing Sheets

Pulse Deposition

○ = M₁
● = M₂
⊕ = M₁ salt
● = M₂ salt

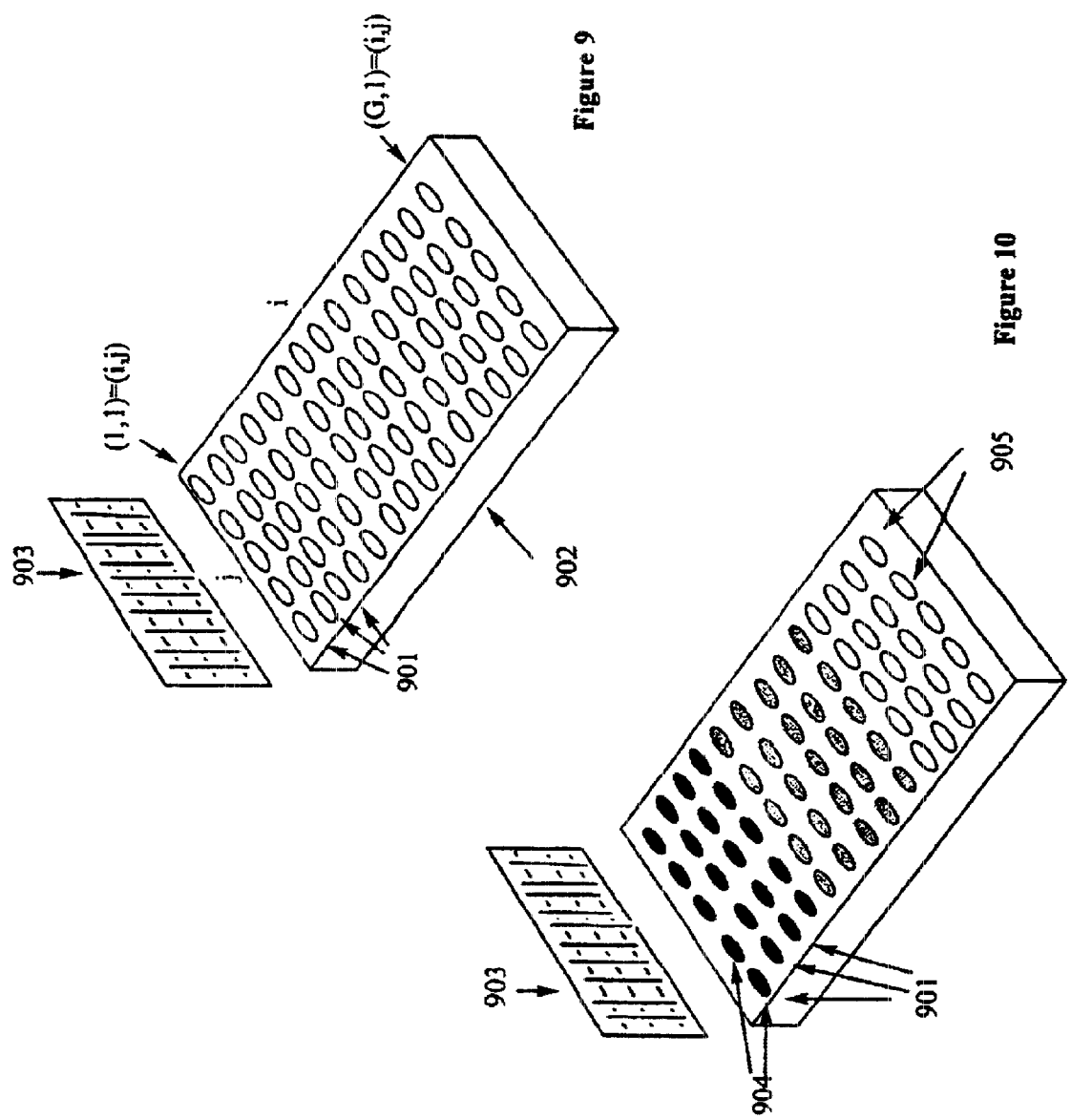

ELECTRODE ARRAY FOR DEVELOPMENT AND TESTING OF MATERIALS

CROSS REFERENCE TO RELATED APPLICATIONS

This application is a continuation-in-part of provisional U.S. patent application Ser. No. 60/113,162, filed Dec. 22, 1998, and a continuation-in-part of provisional U.S. patent application Ser. No. 60/118,067, filed Feb. 1, 1999, the complete disclosures of which are incorporated herein by reference for all purposes.

The United States Government has certain rights in this invention pursuant to Contract No. N00014-99-1-0354 between the U.S. Office of Naval Research and the University of Wyoming.

FIELD OF THE INVENTION

The present invention generally relates to methods and apparatus for the high rate deposition, synthesis and/or analysis of materials on an array of electrodes, and the desired materials developed from the methods. More specifically, the invention is directed to methods of high rate synthesis and/or analysis of an array of materials wherein deposition control techniques in conjunction with the electrode array are employed to develop a meaningful array of materials and to analyze the materials for a desired characteristic to develop one or more materials with the desired characteristics.

BACKGROUND OF THE INVENTION

Developing new and useful materials, in the past, has been by prediction of the general chemistry of compositions and applying known testing methods to a small number of synthesized materials. Even with predicting and applying the currently known chemistry of materials, the number of materials that are predicted in a group is too large to properly analyze. The result of only analyzing a few materials in a predicted group leaves the great majority of predicted useful materials unexplored. Thus, the discovery and development of new materials have need for a method of synthesizing and analyzing new materials with a large number of variable compositions at a high throughput rate.

Combinatorial methods represent a new set of experimental tools that are well suited to explore systems comprised of a very large number of variable compositions. As a consequence of this characteristic, there has been a great deal of recent activity in the application of combinatorial synthesis to drug discovery, *Chem. Rev.* 1997, 97(2), where such large number of variable compositions are commonplace. In cases such as these, a great many different chemical structures need to be examined to find structural motifs, amino acid sequences (e.g. in bioactive polypeptides), or other molecular characteristics that exhibit the desired effect. The key to success in these efforts has been to exploit the power of combinatorial methods both for doing chemical reactions and for examining the efficacy of the resulting compounds, all in a parallel or high-speed serial fashion. The range of types of synthetic schemes and the systems to which they have been applied is typified by the articles in *Chemical Reviews* theme issue (*Chem. Rev.* 1997, 97(2)).

More recently, several groups have begun to apply combinatorial methods to materials problems. An example of this trend is the work being done at UC Berkeley by Schultz et al. To date, these groups have focused predominantly on materials properties, especially luminescence. Also, a recent report by Mallouk et al. points to the use of such methods in electrochemical applications (*Science*, 1998, 280, 1735). Specifically, Mallouk et al. used ink jet processing to deliver multiple metal complexes that served as electrocatalyst precursors to specific sites on a conductive substrate, employed chemical methods to reduce the complexes to produce metallic alloys and then used a novel fluorescence-based method to look for methanol oxidation activity. This appears to be one of the first uses of combinatorial methods in development of electrocatalysts. A particularly useful feature of this method was the demonstration of a parallel testing method. In addition to the efforts described above, several other groups have begun to explore the use of combinatorial methods for synthesis of materials with novel properties (Briceno et al. *Science*, 1995, 270, 273; Kobayashi et al. *J. Am. Chem. Soc.* 1996, 118, 8977).

An electrode's oxidation and reduction capabilities have led to the use of electrodes performing an essential step in synthesizing materials. One of the earliest description of using electrodes in combinatorial synthesis is by Fodor et al. (U.S. Pat. No. 5,424,186). Microelectrodes are used to remove protecting groups in the synthesis of organic molecules. Fodor et al. position an electrode over the protecting group to activate the desired deprotection step. Because of an electrode's versatility and control, the use of an array of electrodes in synthesis and analysis of materials is forthcoming.

In depositing materials onto an electrode many factors contribute to the composition of the material in the array. Some factors even affect the deposited materials in a solution after the material has already been deposited and other compositions are being deposited. In WO98/03521, Weinberg et al. express the need for homogeneous compositions of materials for a meaningful analysis of an array of materials. However, little work has been done to ensure that the array of materials may be analyzed for a desired characteristic and not for unwanted variations in morphology or composition.

An important feature of combinatorial synthesis is the ability to deposit meaningful compositions at discrete electrodes at a high rate of speed. In PCT WO98/14641, the complete disclosure of which is incorporated herein by reference for all purposes, McFarland et al. show an array of electrodes used for combinatorial synthesis and analysis, however, the use of changing out or adding components of the solutions in a solution bath results in an increased number of solutions when a hundred compositions are synthesized. Additionally, when more electrodes are employed to synthesize thousands or ten of thousands of compositions, the number of solutions or additions to solutions needed adversely affects the ability of high-throughput synthesis of compositions. McFarland et al., in WO98/14641, attempt to alleviate the need for a high number of solutions or additions to solution by using a variety of potentials at different electrodes to attempt to adjust the deposition of certain components in the solutions to vary the compositions at the electrodes electronically. While this method may result in a desired library of compositions, the compositions are affected by the method used to deposit and any meaningful analysis or screening is adversely affected by the morphology of the compositions. McFarland et al. discuss how multiple samples of varying composition can be prepared from solutions carrying various metal salts. However, they do not take the necessary steps to produce controllable morphology during the deposition or to maintain the composition of the samples after the deposition. For instance, when electrodepositing metals from solution at overpotentials that vary, a wide variety of surface morphologies are created. Those surface morphologies preclude easy and rapid comparison of the physical or chemical properties of the samples, specifically of the electrochemical, catalytic, or optical properties. Furthermore, when electroplating from solutions that contain Ni, Fe, Cu, and Zn, deposited samples that contain Zn, Ni, or Fe at their surfaces, the Zn, Ni, or Fe will react with the solution-bound salt of Cu to dissolve Zn, Ni, or Fe and deposit Cu. Similar reactions occur between Zn and Ni and between Zn and Fe. This general type of reaction occurs between any two species where the redox state of one species is at a less positive potential than the redox species of another species in the same environment. These reactions inadvertently change the surface compositions and morphologies of the deposits that have been prepared but remain in contact with the precursor-containing solution. Thus, controllable high-throughput synthesis and analysis of new materials using an array of electrodes is not yet feasible.

In order to synthesize and analyze a large number of new materials, a method of developing and analyzing new materials on an array of electrodes employing control techniques to ensure desired compositions and morphologies at known locations on the array is desirable.

SUMMARY OF THE INVENTION

The present invention provides methods and apparatus for the high rate deposition, synthesis and/ or analysis of materials of various compositions onto an array of electrodes, and the materials developed from the methods. In particular, the present invention provides methods of high rate synthesis and/or analysis of an array of materials wherein deposition control techniques in conjunction with the electrode array are employed to develop a meaningful array of materials wherein the array of materials may be analyzed for desired characteristics to develop one or more materials with the desired characteristics.

Array of Electrodes

In order to synthesize a large number of materials with varying compositions, an array of electrodes is employed. The array allows the control necessary for high-throughput synthesis of new materials. The array uses a conducting material to contact two or more discrete conducting regions to produce two or more electronically-discrete electrodes. The array has two or more electronically-discrete electrodes which are addressable individually or collectively, in serial or in parallel, using electronic, optical, or mechanical means, via passive or active, internal or external circuitry. The use of the array of electrodes is preferably by addressing the discrete electrodes individually AND collectively. The electrodes provide an electrical potential or electrical current to initiate deposition of a desired composition at the electrode. The electrodes are controlled by means that allow a predetermined composition to be deposited at a known electrode. Thus, for any given electrode the composition of the material deposited at that electrode is known when the entire array of materials has been synthesized. The electrode array consists of two or more electronically-discrete electrodes, preferably of twenty or more electronically-discrete electrodes, or, more preferably, of 100 or more electronically-discrete electrodes, or, more preferably, of 1000 or more electronically-discrete electrodes, or, more preferably, of 10,000 or more electronically-discrete electrodes, or, most preferably, of 100,000 or more electronically-discrete electrodes.

Deposition

The deposition of materials onto the array of electrodes may be by electrodeposition or co-electrodeposition of one of more elements via reductive or oxidative passage of one or more electrons between the electrodes comprising the array or from some external electrode assembly and the elements, assembly of elements, or chemical or physical assemblies containing the element or elements; electrophoretic deposition of one or more elements via electrostatic interaction between the elements, assembly of elements, or chemical or physical assemblies containing the element or elements and the electrodes comprising the array or from some external electrode assembly; electrochemically-, chemically-, or physically-induced deposition or precipitation of elements, assembly of elements, or chemical or physical assemblies containing the element or elements; or spontaneous precipitation of elements, assembly of elements, or chemical or physical assemblies containing the element or elements.

Deposition may include the introduction of the electrode array into a solution or mixture of components for deposition. Alternatively, the solution or mixture may be introduced to the electrode array. The solution or mixture entrains the components for deposition and supplies the components for deposition onto the electrode when the electrode is addressed in some fashion. The variation of the deposition components in the solution or mixture is controlled to allow a known composition to be deposited at a known electrode. The controlled variation of the deposition components may be achieved by any method wherein the known deposition components are present at the known electrode to deposit the known composition at the electrode.

Deposition may also employ the use of a counter-electrode and reference electrode or simply a counter electrode. The counter-electrode provides current to complete the circuit through the cell. The reference electrode provides for control of the potential applied at the electrode in the array of electrodes.

Control of Deposition

In order to ensure that the array of materials may be meaningfully analyzed, various deposition control techniques are employed. The deposition of materials onto an array of electrodes may lead to varying morphologies amongst the varying materials on the array. One discrete material deposited at one discrete electrode may have an extremely rough surface or morphology compared with the other materials deposited at other electrodes. With some deposition techniques, the morphologies may vary material to material. When analyzing the materials, some desired characteristics are affected by the morphology, and the ability to control morphologies along with other deposition characteristics is highly critical to the analysis of the materials for desired characteristics.

Alternately, the ability to deliberately generate a wide variety of morphologies is highly desirable when such morphologies comprise desired characteristics of the deposits.

The control techniques include methods to adjust or control the morphologies of the depositing or deposited materials, methods to protect the deposited materials from further reactions, methods to control the potential at the electrodes where deposition has occurred, methods to control the exchange of reactive species at deposited materials, methods to control the potential at the depositing material methods to cap or passivate the deposited material, methods to control the current at the electrodes, methods to control the counter-electrode or reference position and other methods to deposit a homogeneous material at discrete electrodes. The control techniques and methods are not limited to the deposition process and may include methods to control or adjust the materials after deposition of all materials on the array. These methods may include additional steps before analysis wherein the materials are processed further to ensure a homogeneous composition at each electrode or one or more homogeneous characteristic at each discrete composition location that is suitable for analysis of the desired characteristic sought.

The methods employed to control the deposition of the materials onto the electrode array include but are not limited to pulse electrodeposition, potential control to avoid exchange reactions, overpotential electrodeposition, the use of kinetically sluggish precursors, the positioning of one or more counter-electrodes or reference electrodes and the use of passivating layers.

Processing

After deposition of the materials on the electrode array an additional step may be employed to further process the materials for analysis. The processing step may occur while the material array is still within contact of the solutions or other components of the deposition step. Processing may include exposure of the array of materials to gaseous, liquid, or solid reactants, controlled heating or cooling of the array of materials, and treatment of the array of materials with electromagnetic radiation of wavelength between $10^{-16}$ m and $10^{-18}$ m.

Analysis

This invention also relates the use of arrays of electrodes as described to analyze materials comprising two or more elements. The array of electrodes may be used to synthesize the array of materials, but the array need not be used to synthesize the materials. Preferably, the array of electrodes is used to synthesize and analyze the array of materials. Methods used to analyze the array of materials may or may not comprise combinations of one or more methods including, but not limited to electrochemical analysis of materials via the electrodes contained in the array or via some external electrode assembly. Other analysis techniques include electrochemical analysis of the materials using electrochemical methods including but not limited to potentiometry, coulometry, voltammetry, and polarography; analysis of the materials via optical methods including but not limited to infrared, Raman, electronic absorption, fluorescence, phosphorescence, and chemiluminescence spectroscopies, atomic spectroscopy, emission spectroscopy based on plasma, arc, and spark atomization, nephelometry, turbidity, refractometry, polarimetry, rotatory dispersion, and circular dichroism; analysis of the materials via x-ray spectroscopies including, but not limited to, x-ray fluorescence, absorption and diffraction spectroscopies; analysis of the materials via electron spectroscopic methods including, but not limited to, x-ray photoelectron spectroscopy, ultraviolet photoelectric spectroscopy, Auger spectroscopy, ion neutralization spectroscopy, electron impact spectroscopy, and penning ionization spectroscopy; analysis of the materials via nuclear magnetic resonance methods including, but not limited to, nuclear magnetic resonance spectroscopy and electron spin resonance spectroscopy; and analysis of the materials via other methods including, but not limited to, radiochemical methods, mass spectrometry, conductometric methods, thermal methods, and chromatographic separations.

BRIEF DESCRIPTION OF THE DRAWINGS

FIG. 5a illustrates the effects of varying the potential while depositing;

FIG. 5b illustrates controlled deposition using overpotential;

FIG. 9 illustrates the positioning of a counter-electrode and a reference electrode;

FIG. 10 illustrates the effect of controlling deposition by the method illustrated in FIG. 9;

DETAILED DESCRIPTION OF THE INVENTION AND PREFERRED EMBODIMENTS

Using arrays of electrodes to synthesize a large number of materials has been shown. Thus far, high rates of synthesis and analysis have not been reached because of the arrays, deposition methods and other factors. In order to exploit the use of large arrays of electrodes in developing materials, control techniques are needed to assist high rates of development and analysis. Employing an array of electrodes without appropriate control of deposition and material properties adversely affects any analysis conducted on the material array. The result of control techniques in developing an array of materials using electrodes is a meaningful array of materials which may be productively analyzed for desired characteristics. By employing control techniques along with the use of the following electrode arrays, deposition steps, processing and analysis, a high rate or high-throughput method and apparatus of synthesizing and analyzing an array of materials is disclosed.

Figure 1:
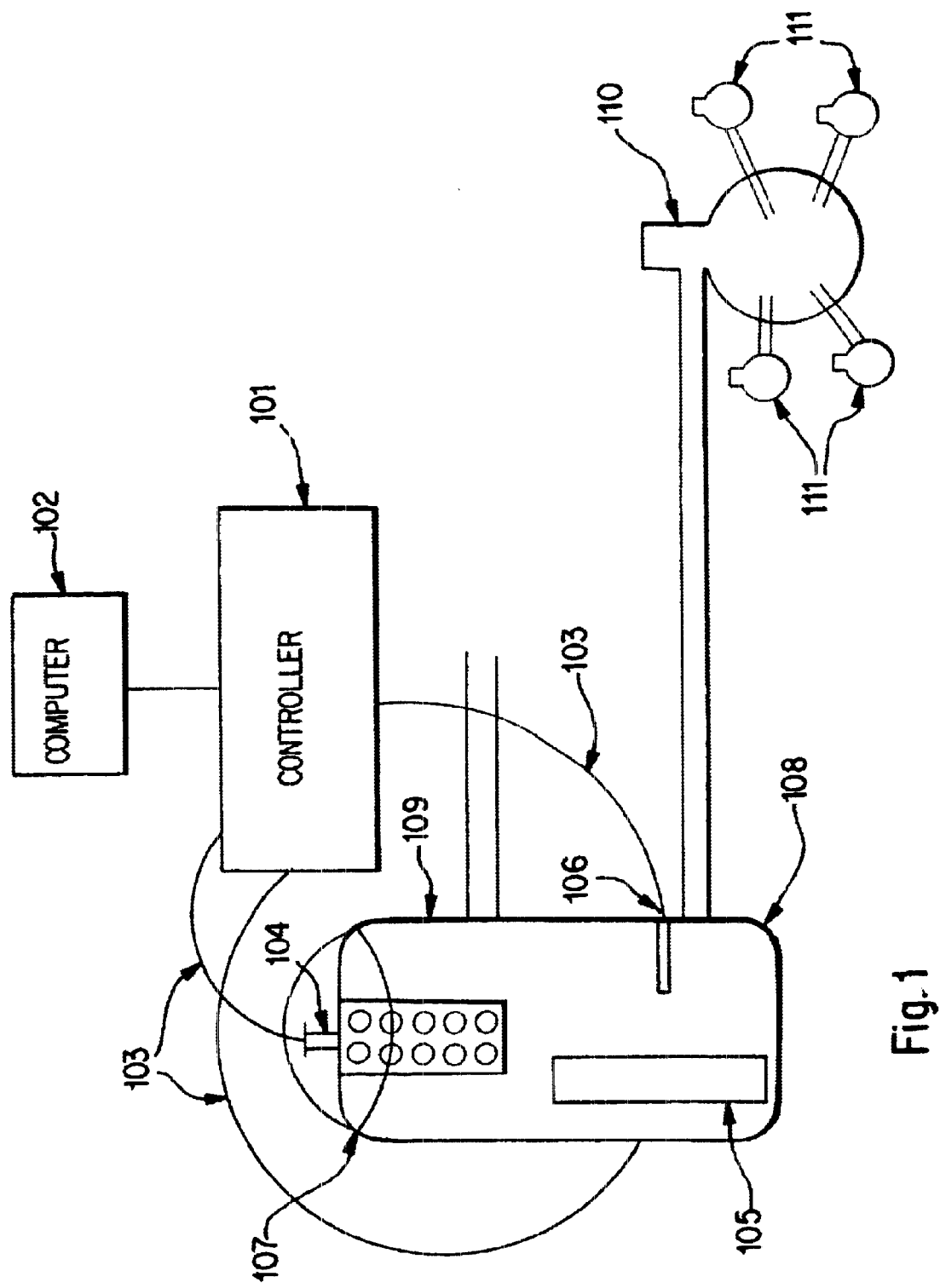
FIG. 1 illustrates a system for high throughput combinatorial synthesis of materials.

The essential elements needed for the high-throughput synthesis and analysis of new materials are depicted in FIG. 1. The system depicted in FIG. 1 includes a controller 101 that is programmed for operation either manually or by computer 102. The controller 101 is connected via wires 103 to the working electrode array 104, the reference electrode (s) 105, and the counter electrode(s) 106. The array of electrodes (the "working" electrode array) 104 is immersed in a container or flow cell 107 through which liquid flows. The liquid contains precursors to electrodeposition and, in some cases, supporting electrolyte salt. The precursors are stored in containers 111. The liquid enters the flow cell 107 through one or more inlet holes 108 and leaves the flow cell 107 through one or more outlet holes 109. The solution is delivered to the flow cell 107 by pressure from a mechanical or other type of pump (not shown). The pump delivers the solution directly to the flow cell 107 or delivers the solution to a mixing chamber 110 which then is pressurized so that solution flows to the flow cell.

Array of Electrodes

In order to synthesize a large number of materials with varying compositions, an array of electrodes is employed. The array allows the control necessary for high-throughput synthesis of new materials. The array uses a conducting material to contact two or more discrete conducting regions to produce two or more electronically-discrete electrodes. The array has two or more electronically-discrete electrodes which are addressable individually or collectively, in serial or in parallel, using electronic, optical, or mechanical means, via passive or active, internal or external circuitry. The use of the array of electrodes is preferably by addressing the discrete electrodes individually AND collectively. The electrodes provide an electrical potential or electrical current to initiate deposition of a desired composition at the electrode. The electrodes are controlled by means that allow a predetermined composition to be deposited at a known electrode. Thus, for any given electrode the composition of the material deposited at that electrode is known when the entire array of materials has been synthesized. The electrode array consists of two or more electronically-discrete electrodes, preferably of twenty or more electronically-discrete electrodes, or, more preferably, of 100 or more electronically-discrete electrodes, or, more preferably, of 1000 or more electronically-discrete electrodes, or, more preferably, of 10,000 or more electronically-discrete electrodes, or, most preferably, of 100,000 or more electronically-discrete electrodes.

Figure 2:
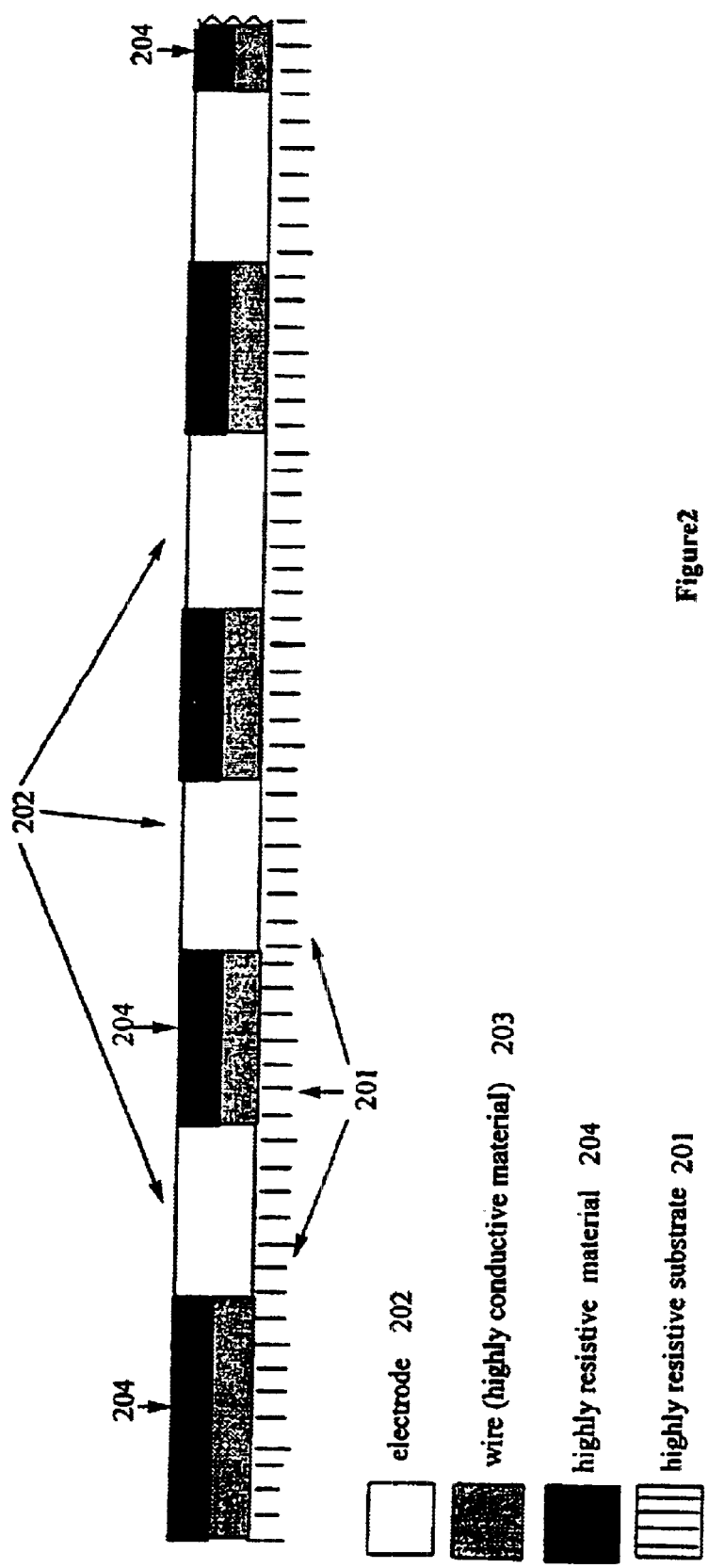
FIG. 2 illustrates a cross section of an electrode array.

A cross section of a typical array used in the high-throughput synthesis and analysis of new materials is shown in FIG. 2. FIG. 2 depicts a highly resistive substrate 201 upon which is located highly conductive electrodes 202. The electrodes are spatially separated to be electronically discrete. Connecting each electrode to the array controller is a highly conductive wire 203. The array controller applies potential and/or current conditions to each highly conductive wire 203 and thus to each highly conductive electrode 202. A highly resistive material 204 is coated on top of or around the wires in order to avoid redox reaction between the wires and the solution. The highly resistive material 204 does not cover the surfaces of the electrodes 202.

An electrode array is composed of discrete highly conductive electrodes, preferably disk-shaped, placed on top of a highly resistive substrate or embedded into the surface of a highly resistive substrate such that the highly conductive electrodes are physically separated from each other. In some cases, the electrodes are connected to an external multiplexing unit such that each electrode can be individually addressed electronically. In other cases, the electrodes are connected to common wires that carry voltage and current signals from the controlling potentiostat to the electrodes. In the latter case, the common wires can number fewer than the electrodes or number the same as the electrodes or number more than the electrodes. Connection of the electrodes to the wires can occur by switched contacts or by permanent contacts. In all cases, the conductive portions of the array of electrodes are completely covered by either an over-coated highly resistive layer or by highly resistive materials that are part of the components, with the exception of the electrode faces, which remain uncovered.

In the preferred embodiment an analog, very large scale integrated circuit (VLSI), complementary metal oxide semiconductor (CMOS), microelectrode array (MEA) chip is used. The MEA is comprised of at least 1,024 microelectrodes that can be addressed individually or grouped, in series or in parallel, and can be used in all of the traditional electrochemical synthetic motifs. This unique platform can be used with high-throughput electrodeposition methodologies that allow production of very large numbers of materials in a very short time.

The MEA electrodes are deposited using traditional silicon fabrication techniques. As such, each microelectrode (measuring less than 100 $\mu$m in diameter) is built on an Al pad deposited on the silicon wafer. After deposition of the typical W/Ti Al diffusion barrier, an overcoat of the desired electrode material is applied, to give functional microelectrodes.

The electrodes may be smaller than 10 $cm^2$, or smaller than 10 $\mu m^2$, or even smaller than 1 $\mu m^2$.

The electrodes can be coupled to single or multiple power supplies, or alternately they can be placed in series with current or power limiting devices (inductors, resistors, etc.). In a preferred embodiment, the array of electrodes can be controlled as to potential and/or current by maintaining multiple wires at multiple potentials and/or currents. The electrodes can then, singly, in groups, or in total, be reversibly switched to the appropriate wire to place the electrode under the desired potential and/or current condition. The switches used to perform this reversible switching operation can include mechanical, electrical, optical, or magnetic materials. For instance, transistors, CMOS, throw switches, etc. can be used for switches. The critical issue is that the potential and/or current condition on each wire is not changed with time during the experiment. Only the electronic circuitry of the system is changed to move electrodes from one wire to another wire. Other embodiments of this controlling and addressing circuitry will be obvious to those skilled in the art.

Deposition

The deposition of materials onto the array of electrodes may be by electrodeposition or co-electrodeposition of one of more elements via reductive or oxidative passage of one or more electrons between the electrodes comprising the array or from some external electrode assembly and the elements, assembly of elements, or chemical or physical assemblies containing the element or elements; electrophoretic deposition of one or more elements via electrostatic interaction between the elements, assembly of elements, or chemical or physical assemblies containing the element or elements and the electrodes comprising the array or from some external electrode assembly; electrochemically-, chemically-, or physically-induced deposition or precipitation of elements, assembly of elements, or chemical or physical assemblies containing the element or elements; or spontaneous precipitation of elements, assembly of elements, or chemical or physical assemblies containing the element or elements.

Deposition may include the introduction of the electrode array into a solution or mixture of components for deposition. Alternatively, the solution or mixture may be introduced to the electrode array. The solution or mixture entrains the components for deposition and supplies the components for deposition onto the electrode when the electrode is addressed in some fashion. The variation of the deposition components in the solution or mixture is controlled to allow a known composition to be deposited at a known electrode. The controlled variation of the deposition components may be achieved by any method wherein the known deposition components are present at the known electrode to deposit the known composition at the electrode.

Deposition may also employ the use of a counter-electrode and reference electrode or simply a counter electrode. The counter-electrode provides current to complete the circuit through the cell. The reference electrode provides for control of the potential applied at the electrode in the array of electrodes.

Figure 3:
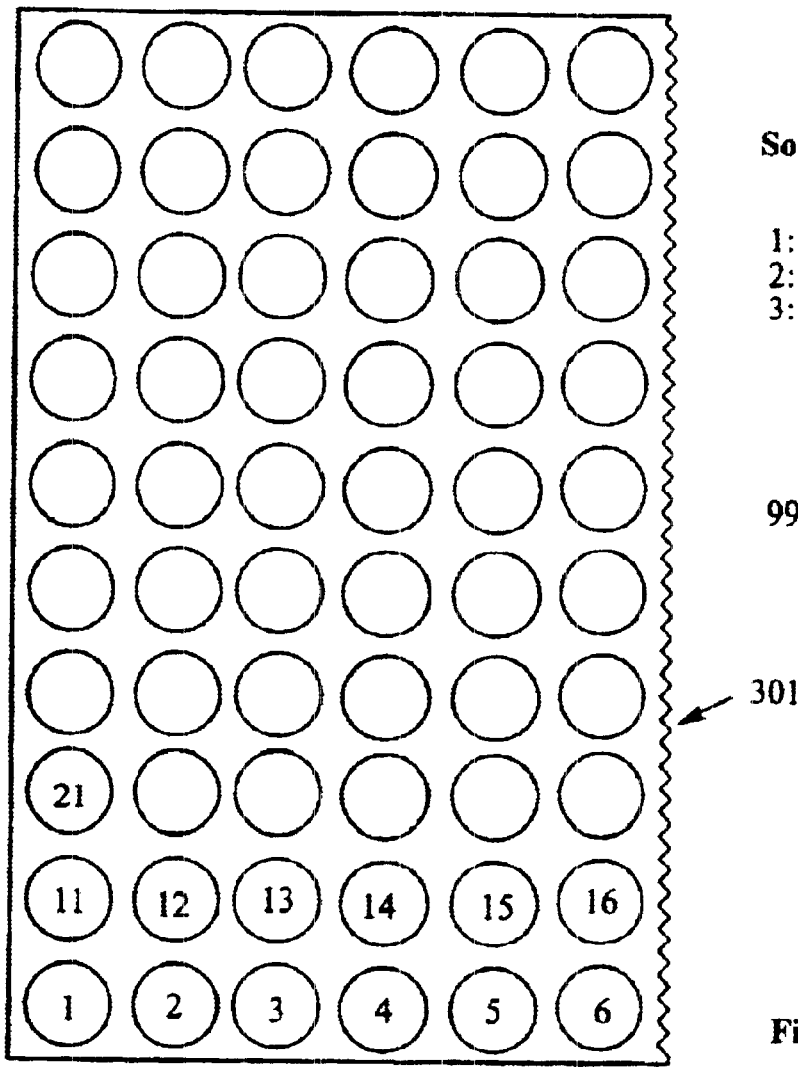
FIG. 3 illustrates an array of addressable electrodes wherein 99 different compositions are obtained during high-throughput combinatorial synthesis.

The spatially-heterogeneous chemical concentration of the precursor in the solution can be varied by varying the input feedstock position and concentration. Thus, in a heterogeneous solution of precursor, an array of electrodes which all electrodeposit at the same time will deposit different materials. In a preferred embodiment, shown in FIG. 3, flowing a solution of regularly (time-based) varying composition (e.g. from 1% X, 99% Y, to 2% X, 98% Y . . . to 99% X, 1%, Y, where X and Y represent different deposition precursors) across an array of electrodes and depositing at a single electrode at a time quickly prepares samples of regularly-varying composition without having to remove the solution or any substantial part of the solution. While the composition of the flowing solution varies slightly over time, at no time does the flowing solution vary significantly across the surface of the array. For example, an array can be placed in a flow cell containing a reference electrode, a counter electrode, and inlet and outlet ports for liquid solution. A deoxygenated 1 liter solution of 1 mM $CuSO_4$ is flowed, during the process, into a mixing chamber containing 1 liter of 1 mM $AgNO_3$. The mixed solution is flowed into the flow cell during the process. Early in the process, the flow cell contains solution that contains primarily $AgNO_3$. Late in the process, the flow cell contains solution that contains primarily $CuSO_4$. Between these extremes, the solution composition changes gradually from mostly $AgNO_3$ to mostly $CuSO_4$. During this change in solution composition, the electrodes in the array of electrodes are biased individually and discretely to one or more potentials that cause deposition of the $CuSO_4$ and/or $AgNO_3$. After deposition at one electrode, that electrode is returned to a neutral potential and another electrode is turned "on" at a depositing potential. This "serial deposition" is continued until all electrodes have been so treated. The result of this experiment is an array of deposited samples of regularly-varying composition suitable for collection, treatment, and/or analysis.

Control of Deposition

In order to ensure the array of materials may be meaningfully analyzed, various deposition control techniques are employed. The deposition of materials onto an array of electrodes may lead to varying morphologies amongst the varying materials on the array. One discrete material deposited at one discrete electrode may have an extremely rough surface or morphology compared with the other materials deposited at other electrodes. With some deposition techniques, the morphologies may vary material to material. When analyzing the materials, some desired characteristics are affected by the morphology, and the ability to control morphologies along with other deposition characteristics is highly critical to the analysis of the materials for desired characteristics.

Alternately, the ability to deliberately generate a wide variety of morphologies is highly desirable when such morphologies comprise desired characteristics of the deposits.

The control techniques include methods to adjust or control the morphologies of the depositing or deposited materials, methods to protect the deposited materials from further reactions, methods to control the potential at the electrodes where deposition has occurred, methods to control the exchange of reactive species at deposited materials, methods to control the potential at the depositing material, methods to cap or passivate the deposited material, methods to control the current at the electrodes, methods to control the counter-electrode and other methods to deposit a homogeneous material at discrete electrodes. The control techniques and methods are not limited to the deposition process and may include methods to control or adjust the materials after deposition of all materials on the array. These methods may include additional steps before analysis wherein the materials are processed further to ensure a homogeneous composition at each electrode or one or more homogeneous characteristic at each discrete composition location that is suitable for analysis of the desired characteristic sought The methods employed to control the deposition of the materials onto the electrode array include but are not limited to pulse electrodeposition, potential control to avoid exchange reactions, overpotential electrodeposition, the use of kinetically sluggish precursors, the positioning of one or more counter-electrodes and the use of passivating layers.

Controlling the electronic state of the reference electrode can act to vary the potential at different electrodes, which can act to vary the composition and/or thickness of deposits at those electrodes. Additionally, varying the physical location of the counter electrode can vary the real current density at each electrode surface for a number of electrodes that are held at the same total and apparent current density. For example, as shown in FIGS. 9–12, for an array of electrodes 902 where every electrode 901 is held at a potential that can initiate one or more redox events with solution species at rates determined by the individual current densities across each electrode 901, said current densities can be varied across the array of electrodes 902 merely by positioning the counter electrode 903 closer to one part of the array than to other parts of the array. Varying said current densities in this manner results in making thicker deposits 904 at the electrodes 901 nearer the counter electrode 903 compared to thinner deposits 905 made at the electrodes 901 farther from the counter electrode. This provides a ready mechanism to control the gross amount of material electrodeposited onto a particular electrode. Depositing other samples on top of said material then allows both compositional and structural control over the total sample prepared at a particular electrode.

Pulse electrodeposition techniques can be used in combination with arrays of electrodes to prepare libraries of samples that have similar or nearly identical surface morphologies. For example, an array of electrodes can be placed into a solution containing elecrodeposition precursors. One or more electrodes can then be placed under potential control in such a way that the electrodeposition precursors are reacted to form deposits on the electrodes. Such reaction can occur by reducing the Fermi level (or "potential") of the electrodes until electrons pass from the electrodes to the precursors, where that electron transfer is accompanied by deposition of the desired composition.

Typically, such "reductive deposition" as described above results in deposits with widely varying morphologies that depend on precursor concentration, movement of the solution, temperature, and potential. Such variations in morphology introduce considerable difficulty when comparing the physical and chemical properties of the deposits.

Figure 4:
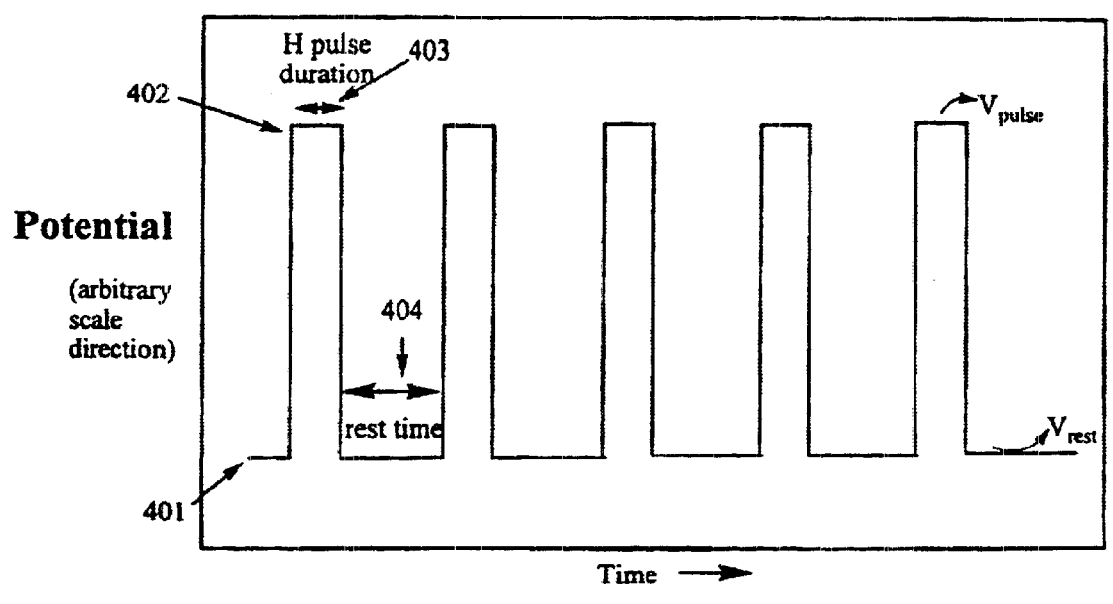
FIG. 4 illustrates a control technique of pulse electrodeposition.

In the present invention, the morphologies of the deposits that are prepared onto the array of electrodes may be controlled to be similar or dissimilar by using pulse electrodeposition. Pulse electrodeposition methods involve pulsing the potential to regions where the precursors are reduced, followed by returning to a potential region where little reaction occurs. FIG. 4 shows the potential vs time plot typical of a pulse electrodeposition synthesis process cycle. The starting potential 401, pulse potential 402, pulse duration 403 and rest time 404 between pulses can be controlled to provide the morphology required.

For example, an array of 1024 electrodes that are individually controlled and held at +0.5 volts (V) (vs. the standard electrochemical reference redox couple of Ag/AgCl) by computer can be placed into a water solution that contains one molar concentration of electrolyte $NaNO_3$, one millimolar concentration of electrodeposition precursor $CuSO_4$, and one millimolar concentration of electrodeposition precursor $AgNO_3$. The computer can be insructed to change the potential of one electrode from +0.5 V to −0.3 V and then to hold the potential at that value for 0.01 seconds. The computer can then be instructed to change the potential from −0.3 V to +0.5 V and then to hold the potential at that value for 0.09 seconds. The computer can be instructed to impose this potential/time "pulse" waveform multiple times ("cycles") onto the electrode until the electrode is covered by a sample of suitable thickness. The computer can then be instructed to perform identical (or different) waveforms onto a second electrode until another deposit is formed.

Preferably, the pulse duration is of sufficient time to deposit most of the precursors in the diffusion layer but not of sufficient time to deposit precursors which encounter the surface through mass transport processes. Likewise, the rest duration is preferably of sufficient time to allow the precursor dissolved in the bulk solution (i.e. away from the electrode) to repopulate the diffusion layer. Typical values for these durations are pulse durations of less than 100 seconds, more preferably pulse durations of less than 10 seconds, more preferably pulse durations of less than 1 second, more preferably pulse durations of less than 0.1 seconds, more preferably pulse durations of less than 0.01 seconds, more preferably pulse durations of less than 0.001 seconds, more preferably pulse durations of less than 0.0001 seconds, more preferably pulse durations of less than 0.00001 seconds, or most preferably pulse durations of less than 0.000001 seconds. Typical values for the rest durations include rest durations of less than 100 seconds, more preferably rest durations of less than 10 seconds, more preferably rest durations of less than 1 second, more preferably rest durations of less than 0.1 seconds, more preferably rest durations of less than 0.01 seconds, more preferably rest durations of less than 0.001 seconds, more preferably rest durations of less than 0.0001 seconds, more preferably rest durations of less than 0.00001 seconds, or most preferably rest durations of less than 0.000001 seconds.

In order to prepare deposits of varying atomic composition, the relative concentrations of the electrodeposition precursors can be varied after preparation of one deposit on one electrode and before preparation of a second deposit on a second electrode. For instance, a deposit can be formed at one electrode from a 1:1 molar ratio solution of $CuSO_4$ and $AgNO_3$ and a deposit of different composition can be formed at a second electrode from a 2:1 molar ratio solution of $CuSO_4$ and $AgNO_3$.

This invention provides at least two unexpected advantages: the use of pulse electrodeposition with an array of electrodes minimizes variations in morphologies observed when preparing multiple samples and allows ready comparison of chemical and physical properties of the samples; and the use of an array of electrodes with pulse electrodeposition allows the electrochemical variables used in the pulse electrodeposition such as starting potential, pulse potential, pulse duration, rest time, temperature, electrolyte concentration, relative and combined concentrations of the precursors, and number of cycles to be varied for different deposits in order to affect the physical and chemical characteristics of the deposits.

Processing

After deposition of the materials on the electrode array an additional step may be employed to further process the materials for analysis. The processing step may occur while the material array is still within contact of the solutions or other components of the deposition step. Processing may include exposure of the array of materials to gaseous, liquid, or solid reactants, controlled heating or cooling of the array of materials, and treatment of the array of materials with electromagnetic radiation of wavelength between $10^{-16}$ m and $10^{-8}$ m.

Analysis

This invention also relates the use of arrays of electrodes as described to analyze materials comprising two or more elements. The array of electrodes may be used to synthesize the array of materials, but the array need not be used to synthesize the materials. Preferably, the array of electrodes is used to synthesize and analyze the array of materials. Methods used to analyze the array of materials may or may not comprise combinations of one or more methods including, but not limited to electrochemical analysis of materials via the electrodes contained in the array or via some external electrode assembly. Other analysis techniques include electrochemical analysis of the materials using electrochemical methods including but not limited to potentiometry, coulometry, voltammetry, and polarography; analysis of the materials via optical methods including but not limited to infrared, Raman, electronic absorption, fluorescence, phosphorescence, and chemiluminescence spectroscopies, atomic spectroscopy, emission spectroscopy based on plasma, arc, and spark atomization, nephelometry, turbidity, refractometry, polarimetry, rotatory dispersion, and circular dichroism; analysis of the materials via x-ray spectroscopies including, but not limited to, x-ray fluorescence, absorption and diffraction spectroscopies; analysis of the materials via electron spectroscopic methods including, but not limited to, x-ray photoelectron spectroscopy, ultraviolet photoelectric spectroscopy, Auger spectroscopy, ion neutralization spectroscopy, electron impact spectroscopy, and penning ionization spectroscopy; analysis of the materials via nuclear magnetic resonance methods including, but not limited to, nuclear magnetic resonance spectroscopy and electron spin resonance spectroscopy; and analysis of the materials via other methods including, but not limited to, radiochemical methods, mass spectrometry, conductometric methods, thermal methods, and chromotographic separations.

Once prepared, the array of samples can be examined for chemical reactivity (such as corrosion, poisoning by carbon monoxide, sulfur or other catalyst poisons, or other types of chemical reactions), electrochemical activity, catalytic or electrocatalytic activity toward a solution-bound species, conductivity, morphology, surface area, surface composition, bulk composition, thickness, presence of interfacial layers (such as metal oxide films or mixed metal oxide films), thickness of such layers, and other properties of relevance to the desired application, including the dependence of the properties above on temperature, pressure and solution composition. In order to examine the samples for properties which involve redox events or charging (e.g. non-Faradaic) events, the array is "strobed" with an interrogating potential or current or combination. While each sample is interrogated, the resulting potential or current or combination of the two is monitored. A preferred embodiment is where the potential or current or combination of the two is strobed across the array of samples at a rate of more than ten samples per one hundred seconds, or more preferably at a rate of more than ten sample per ten seconds, or more preferably at a rate of more than ten samples per one second, or more preferably at a rate of more than ten samples per 0.1 second, or more preferably at a rate of more than ten samples per 0.01 seconds, or more preferably at a rate of more than ten samples per 0.001 seconds, or more preferably at a rate of more than ten samples per 0.0001 seconds, or most preferably at a rate of more than ten samples per 0.00001 seconds. In a typical experiment, the potentiostat is directed to impose a constant current across one sample while the potential of the sample, referenced to a reference electrode in solution and charge balanced by a counter electrode in solution, is monitored. The sample is then returned to near zero current and the potentiostat is directed to perform a similar "polarization" experiment on another sample. This interrogation is continued until the performances of all of the desired samples have been examined. In another typical experiment, the potentiostat is directed to apply constant or varying potentials across a set of samples in a high-speed serial manner while the resultant currents are likewise monitored and recorded.

Morphology

The control of the surface morphologies of the deposited compositions is critical to any meaningful analysis or screening of the compositions for desired properties or characteristics. Variations in morphology may occur at different electrodes when conditions are not constant for each deposition step for different electrodes. Such variations in morphology introduce considerable difficulty when comparing the physical and chemical properties of the deposits. A first composition with a first morphology may show exceptional properties when analyzed or screened yet the first composition may still have inferior properties or characteristics compared to other compositions on the electrode array with a different morphology then the first morphology. Likewise, an array of samples that all possess rough morphologies may exhibit anomalous characteristics in total when compared to bulk or smooth samples. By controlling the morphologies of all of the compositions on the array the screening or analyzing process more readily identifies the composition with the desired properties or characteristics.

Another way of controlling the morphology of the depositions employs the use of a test macroelectrode array. The macroelectrode array allows the electrochemistry for a class of compositions to be explored with fewer yet larger electrodes. This provides a convenient amount of deposit to be prepared, enabling easy and rapid analysis of the chemical and physical characteristics of the deposit, including surface morphology, thickness, composition, compositional distribution (i.e. homogeneity), etc. This information can then be used to determine experimental conditions used in preparing an array of samples onto an array of electrodes.

Pulse Electrodeposition

Pulse electrodeposition techniques can be used in combination with arrays of electrodes to prepare libraries of samples that have similar or dissimilar surface morphologies. For example, an array of electrodes can be placed into a solution containing electrodeposition precursors. One or more electrodes can then be placed under potential control in such a way that the electrodeposition precursors are reacted to form deposits on them. Such reaction can occur by reducing the Fermi level (or "potential") of the electrodes until electrons pass from the precursors into the electrodes, where that electron transfer is accompanied by deposition of the product deposit.

In a typical situation, such "reductive deposition" as described above results in deposits with widely varying morphologies that depend on precursor concentration, movement of the solution, temperature, and potential.

In the present invention, the morphologies of the deposits that are prepared onto the array of electrodes are controlled to be similar or dissimilar by using pulse electrodeposition. This method is particularly suited to preparation of samples with fairly smooth surfaces. This method involves pulsing the potential to regions where the precursors are reduced, followed by returning to a potential region where little reaction occurs. FIG. 1 shows the potential vs time plot typical of a pulse electrodeposition synthetic experiment. The starting potential, pulse potential, pulse duration and rest time between pulses can be controlled to provide the morphology required.

For example, an array of 1024 electrodes that are individually controlled and held at +0.5 volts (V) (vs. the standard electrochemical reference redox couple of Ag/AgCl) by computer can be placed into a water solution that contains one molar concentration of electrolyte $NaNO_3$, one millimolar concentration of electrodeposition precursor $CuSO_4$, and one millimolar concentration of electrodeposition precursor $AgNO_3$. The computer can be instructed to change the potential of one electrode from +0.5 V to –0.3 V and then to hold the potential at that value for 0.01 seconds. The computer can then be instructed to change the potential from –0.3 V to +0.5 V and then to hold the potential at that value for 0.09 seconds. The computer can be instructed to impose this potential/time "pulse" waveform multiple times ("cycles") onto the electrode until the electrode is covered by a sample of suitable thickness. The computer can then be instructed to perform identical (or different) waveforms onto a second electrode until another deposit is formed.

In order to prepare deposits of varying atomic composition, the relative concentrations of the electrodeposition precursors can be varied after preparation of one deposit on one electrode and before preparation of a second deposit on a second electrode. For instance, a deposit can be formed at one electrode from a 1:1 molar ratio solution of $CuSO_4$ and $AgNO_3$ and a deposit of different composition can be formed at a second electrode from a 2:1 molar ratio solution of $CuSO_4$ and $AgNO_3$.

This invention provides at least two unexpected advantages: the use of pulse electrodeposition with an array of electrodes minimizes variations in morphologies observed when preparing multiple samples and allows ready comparison of chemical and physical properties of the samples; and the use of an array of electrodes with pulse electrodeposition allows the electrochemical variables used in the pulse electrodeposition such as starting potential, pulse potential, pulse duration, rest time, temperature, electrolyte concentration, relative and combined concentrations of the precursors, and number of cycles to be varied for different deposits in order to learn how they affect the physical and chemical characteristics of said deposits.

Potential Control to Avoid Exchange Reactions

Figures 6A, 6B:
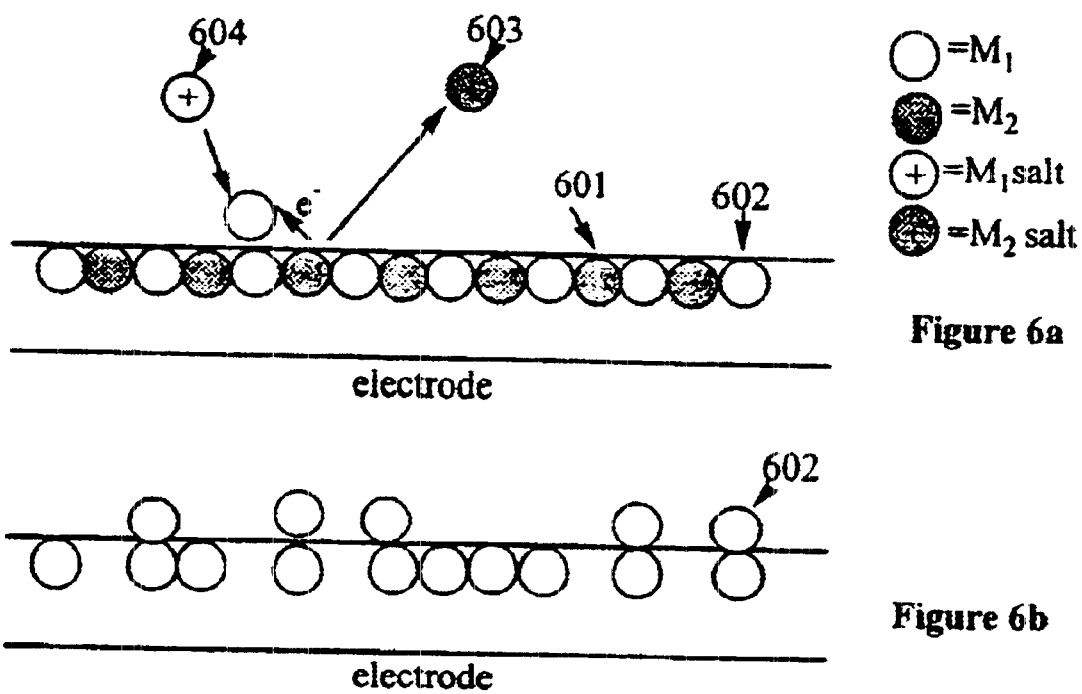
FIG. 6a illustrates the process of exchange reactions.
FIG. 6b illustrates the result of an exchange reaction.

When electrodepositing samples that contain two or more metals from solutions that contain two or more electrodeposition precursors, the deposits react with the precursors to degrade or change the deposit surface composition, surface morphology, and other characteristics. This reaction, illustrated in FIG. 6a, occurs between deposited atoms 601 & 602 and the precursor(s) 603 & 604. The deposited type of atoms that possess less positive redox potentials 601 than the Fermi levels of the precursor(s) 604 are involved in an exchange reaction. The deposited types of atoms that posses more positive redox potentials 602 remain unaffected by the associated precursor 604. The type of atoms with less positive redox potentials 601 exchange with the precursor(s) 604 which results in a deposit having only one type of atom at the surface of the deposit as shown in FIG. 6b. For example, a deposit of copper and silver placed in a solution containing copper salt and silver salt will spontaneously and preferentially reduce silver from the salt to give silver metal at the deposit while dissolving copper salt from the electrode. This event interferes with clear and efficient control over electrodeposition used to prepare the composition and morphology sample.

Figure 7:
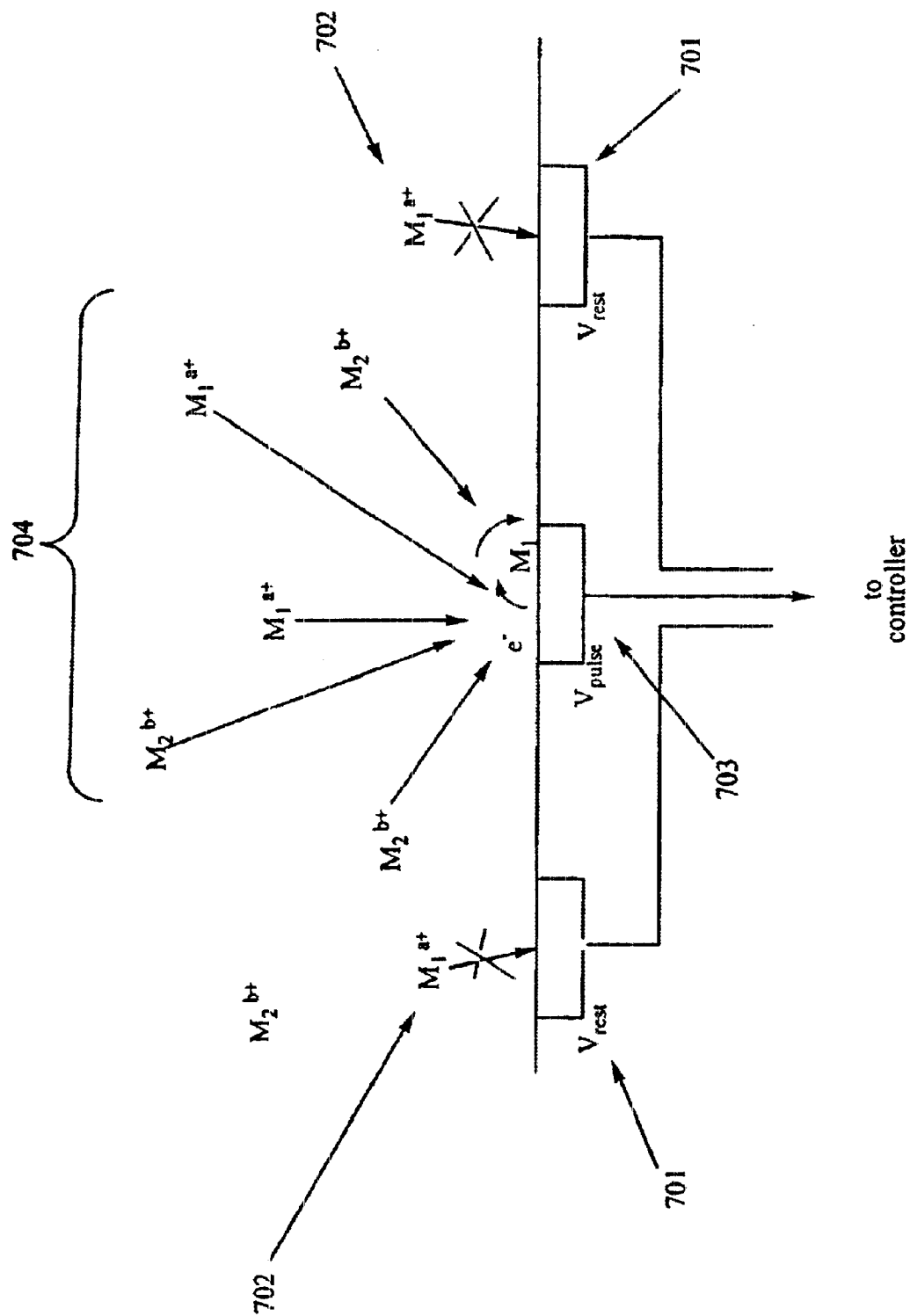
FIG. 7 illustrates the control of potential to reduce exchange reactions.
Figure 8:
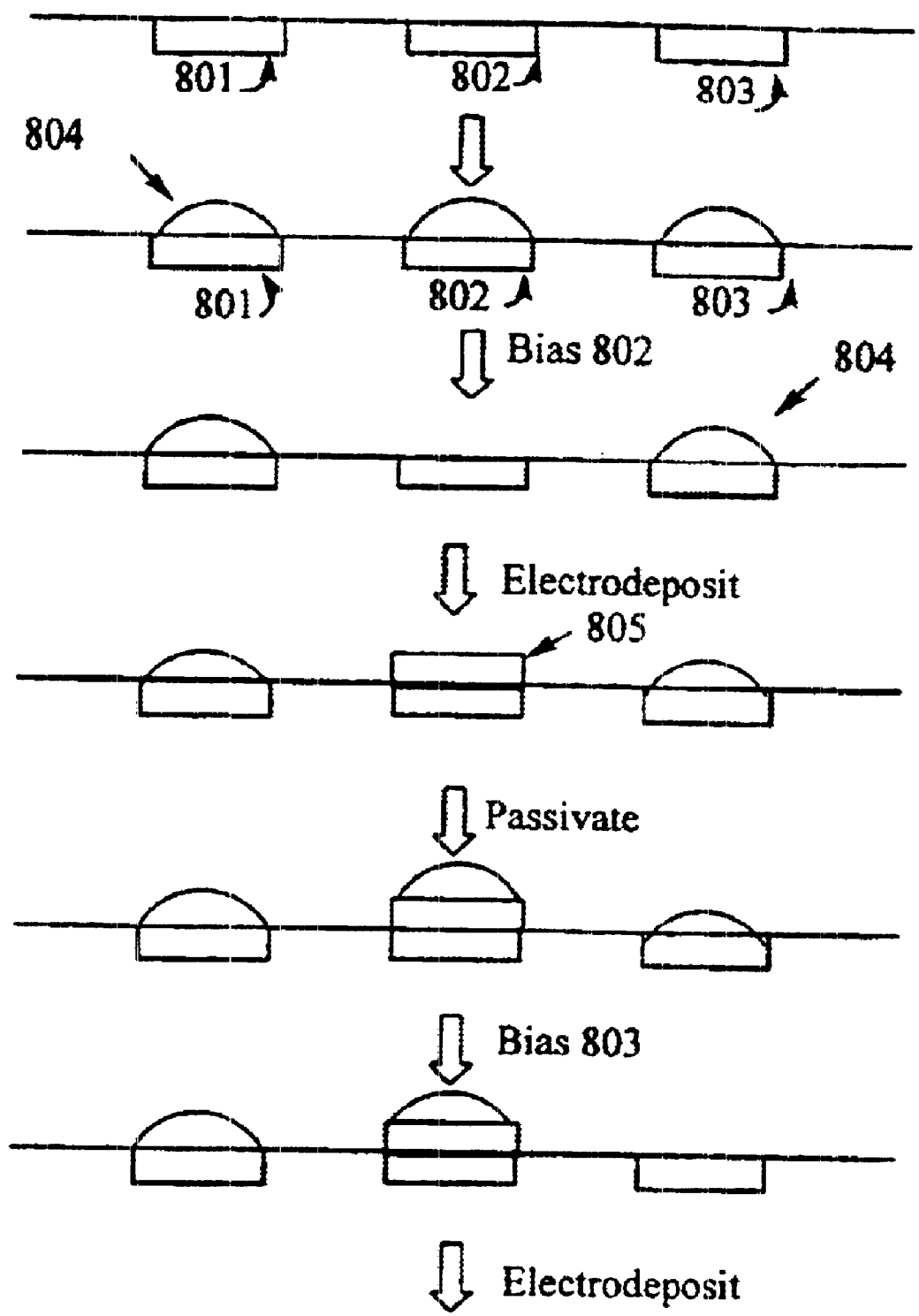
FIGS. 8a–f illustrate the use of passivating layers.
Figure 11:
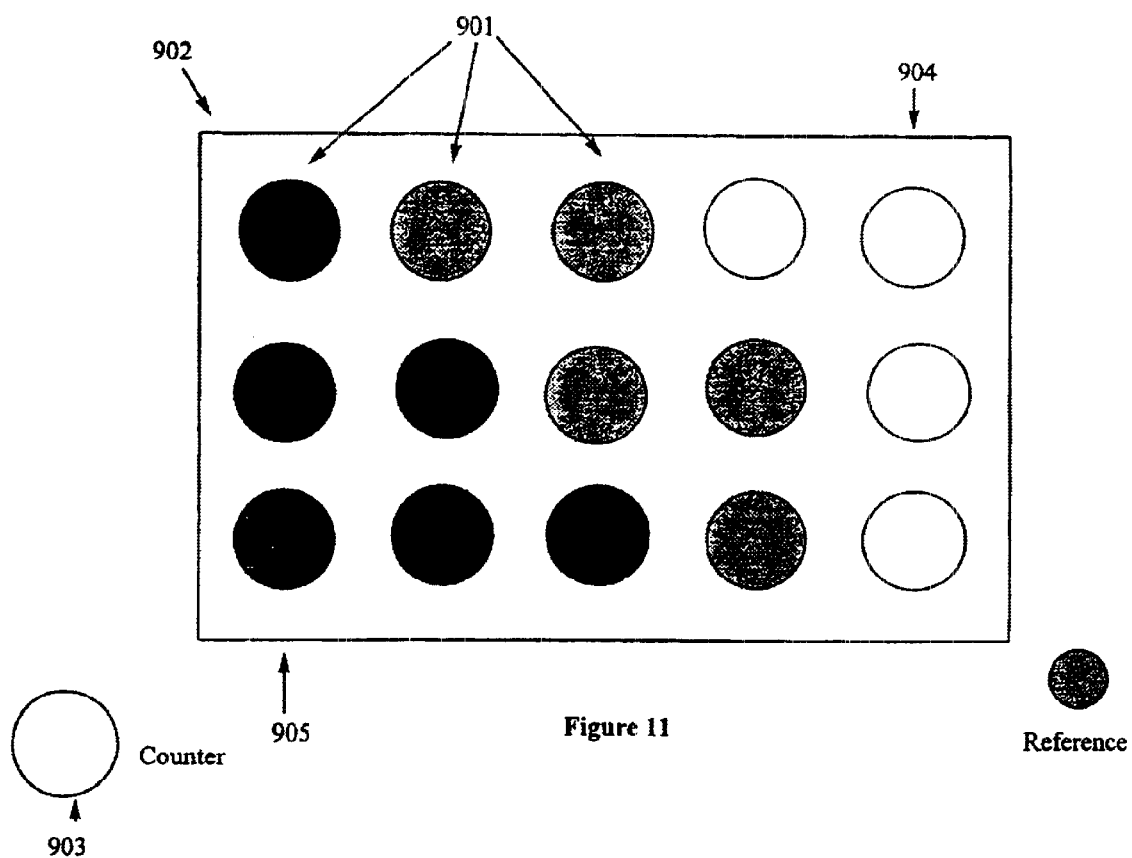
FIG. 11 illustrates an overview of the positioning of a counter-electrode and a reference electrode.
Figure 12:
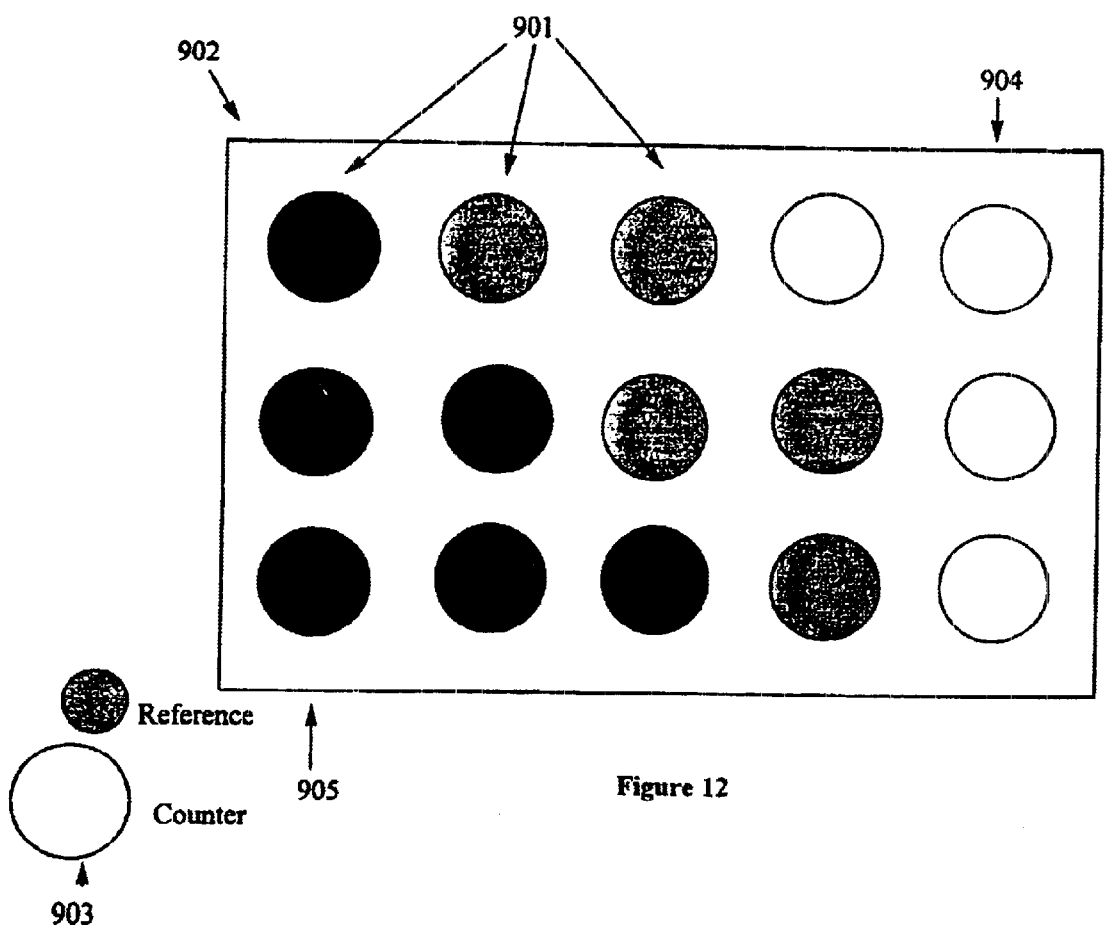
FIG. 12 illustrates an overview of the effect of controlling deposition by the method illustrated in FIG. 11.

The present invention describes a method whereby the array of electrodes is held under potential control by the potentiostatic device at all time during the synthesis, processing and analysis of an array of samples deposited onto the array of electrodes. As shown in FIG. 7, the electrodes 701 with deposits of materials are supplied with a potential to control the exchange reaction of precursor 702, while the addressed electrode 703 has the desired deposition reaction 704 taking place. This potential control avoids uncontrolled reaction between the deposits and the precursors in solution.

An unexpected benefit of this invention include the ability to prepare arrays of materials onto arrays of electrodes where the materials have compositions and morphologies that are a result of the electrodeposition method employed and not of uncontrolled side reactions.

Overpotential Electrodeposition

Nucleation of electrodeposits occurs by reduction of an electrodeposition precursor to give a reaction product and attachment of the product to the electrode surface. Growth of electrodeposits occurs by reduction of an electrodeposition precursor to give a reaction product and attachment of the product to the previously deposited material.

Figure 5:
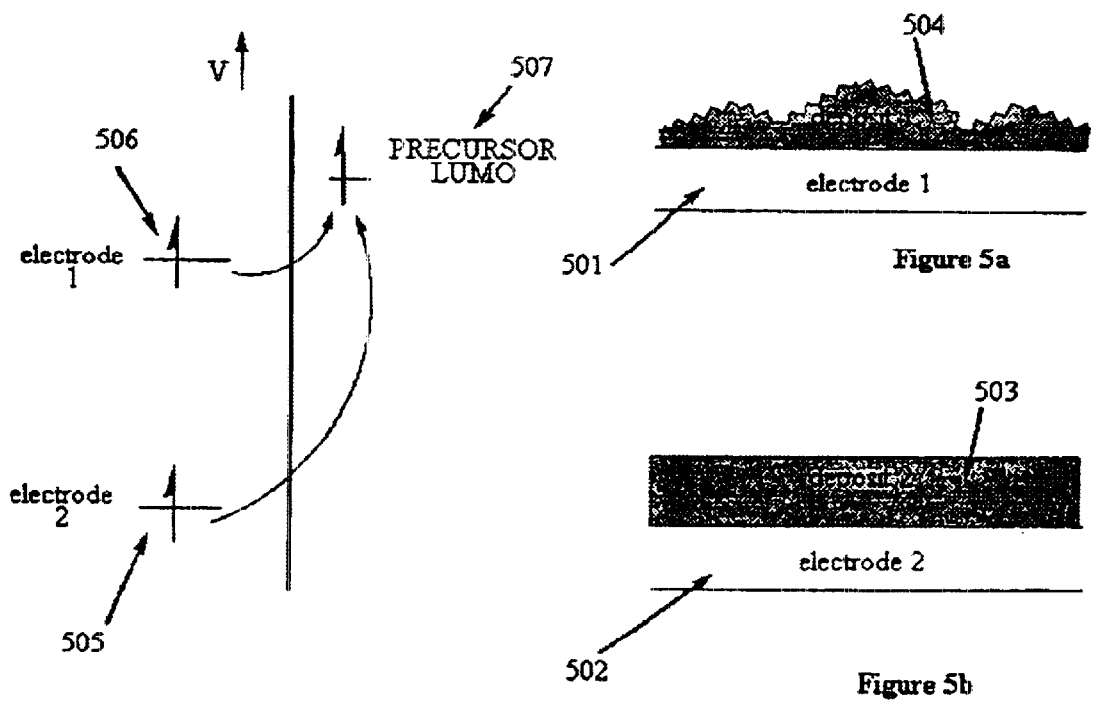
FIG. 5 illustrates two potentials in deposition.

As shown in FIGS. 5 & 5a, if the electrode potential 506 used at an electrode 501 to reduce the electrodeposition precursor is the same or similar to the standard reduction potential 507 of that precursor, most electrodeposition occurs by growth onto fewer nucleation sites. Deposits 504 prepared in this manner typically exhibit rough surface morphologies.

As shown in FIG. 5b, if the electrode potential 505 used at an electrode 502 to reduce the electrodeposition precursor is much less than the standard reduction potential 507 of that precursor, most electrodeposition occurs by nucleation at the nearest surface. Deposits 503 prepared in this manner typically exhibit smooth surface morphologies.

This invention describes a method that is comprised of the use of an array of electrodes and a method of electrodeposition whereby the potential of each electrode is controlled so that preparation of deposits with identical, similar, or different compositions and similar or dissimilar surface morphologies is enabled. An unexpected benefit of this method is that ready comparison of the physical and chemical properties of the deposits is possible without adjustment for real or perceived variations in morphology between deposits.

Use of Kinetically Sluggish Precursors

When electrodepositing samples that contain two or more metals from solutions that contain two or more electrodeposition precursors, the deposits react with the precursors to degrade or change the deposit surface composition, surface morphology, and other characteristics. This reaction, illustrated in FIGS. 6a & 6b, occurs between deposited types of atoms that possess less positive redox potentials than the Fermi levels of the precursor(s). For example, a deposit of platinum and silver placed in a solution containing platinum salt and silver salt will spontaneously and preferentially reduce silver from the salt to give silver metal at the deposit while dissolving platinum salt from the electrode. This event interferes with clear and efficient control over electrodeposition used to prepare the composition and morphology sample.

The present invention describes a method whereby kinetically sluggish redox species are employed as the electrodeposition precursors. The use of such species for this application is both novel and of great utility. In this method, the spontaneous reaction between some or all of the deposited material and the precursors in solution is significantly slowed by employing kinetically sluggish precursors. Thus, electrochemical reaction between the deposit and a precursor occurs only when the reaction is initiated by a deliberately-applied overpotential at the deposit.

An unexpected benefit of this invention include the ability to now prepare arrays of samples onto arrays of electrodes where the samples have compositions and morphologies that are a result of the electrodeposition method employed and not of uncontrolled side reactions. Another unexpected benefit of this invention include the ability to now prepare arrays of samples onto arrays of electrodes where the samples can remain in solutions containing the precursors without degradation. This ability enables ready preparation of samples of more than one composition.

Passivating Layers

An additional control technique is the use of passivating layers to prevent deposits from reacting with solution phase components or precursors. Such passivating layers are made of materials that can be electrochemically grown and removed. Thus, the use of potential control can effect the availability (or lack of it) of a given layer.

As shown in FIGS. 8a–f, the electrodes 801, 802 & 803 are immersed in a solution containing the passivating agent(s) and the desired precursors. The electrodes 801–803 are first passivated by the passivating agent(s) to form passivating layers 804. The electrode 802 is then biased to remove the passivating layer 804. The deposition of the desired composition 805 then occurs at electrode 802. The electrode 802 is then passivated again with a passivating layer 804 where the desired composition 805 is also protected by the passivating layer 804. The next electrode 803 to be deposited is then biased to remove the passivating layer 804 and addressed for deposition. The steps of biasing an electrode, depositing a desired composition and passivating the electrode and composition are repeated for the entire array.

Examples of passivating agents are self-assembled monolayers, oxides and electropolymerized films. Self-assembled monolayers attach to every electrode and passivate the entire array of electrodes. A single passivating agent or combinations of passivating agents may be used. These agents can include thiols, pyridine and its derivatives, amine or thiol terminated dendrimers, etc. The passivation layer is removed from the electrode where the next deposition is desired via electrochemical hydrogen or oxygen evolution via a chemical desorption step.

For metals that form stable, blocking (i.e. relatively passive) oxide films, the oxide is electrochemically formed via oxidation of the deposit in aqueous solution. Then, that deposit is not available for further deposition chemistry until the oxide has been purposefully reduced. The deposition solution conditions are typically oxidizing, so spontaneous and uncontrolled reduction of these oxide films in such solutions is not likely.

An electropolymerized films is used to block the surface toward any further chemistry until the layer is removed (e.g. electrochemically or via laser irradiation, photochemically or via ablation). Oxidation of phenol is a preferred example, because it is a self-healing passivating film (if a spot is left uncoated, phenol gets in and is oxidized to block that spot). Vigorous gas evolution is employed to remove the passivating layer. Another embodiment is to drain the flow cell, then irradiate a given spot with UV (through a quartz widow) and ablate the film off of the metal surface.

Use of an Array of Electrodes to Prepare, Process, and Assay an Array of Samples An array of electrodes that is controlled by a multiplexed potentiostat instrument can be placed into solution. Typically, the array of electrodes is comprised of fifty or more electrodes, or more preferably 100 or more electrodes, or more preferably 1000 or more electrodes, or more preferably 10,000 or more electrodes, or most preferably 100,000 or more electrodes.

The solution is comprised of one or more species that are affected by electrochemistry. For example, a species can be affected by removing one or more electrons from it, by adding one or more electrons to it, by applying a potential across it, by changing the conditions of the solution near the electrode such that these conditions lead to the deposition of the species from solution, or by similarly affecting solvent or other species that interact in some manner with the species.

Specifically, one manner in which a species can be affected involves using an electrode to remove one or more electrons from a species or add one or more electrons to a species so that the species precipitates from solution onto the electrode. This event is termed electrodeposition.

As an example of an experimental context suitable for electrodeposition, the array could be immersed in a solution that contains 1 mM of a metal salt such as $CuSO_4$. Typically, the solution will also contain 1 M of an electrolyte salt such as $NaNO_3$, although this is not necessary.

As another example of an experimental context suitable for electrodeposition, the array could be immersed in a solution that contains 1 mM of a metal salt such as $CuSO_4$ and 1 mM of another metal salt such as $AgNO_3$. Other contexts suitable for electrodeposition include those where the number of metal salts is more than two, those where the relative concentrations of the metal salts are varied from 1 M to 0.000001 mM, those where the electrolyte concentration is varied from 5 M to 0.001 mM, and those where other experimental variables (such as temperature, movement of the solution, type of solvent, etc.) are controlled to provide additional conditions for electrodeposition.

One preferred experimental context is to immerse an array of 1024 electrodes into a water solution containing 1 M $NaNO_3$, 0.5 mM $CuSO_4$, and 0.5 mM $AgNO_3$. The solution is contained in a "flow cell" that mechanically holds the array in place and provides inlet and outlet tubes to flow the solution across the array of electrodes. The flow cell also contains mechanical devices (holes) that allow inclusion of a counter electrode and a reference electrode. Neither electrode is included as a part of the array. Alternately, the reference electrode can be included as a part of the array. The counter electrode is fabricated to be of high surface area and positioned so that the electrochemical events occur similarly across the array. One or more electrodes in the array are used in conjunction with the counter and reference electrodes to perform electrochemistry at the one or more electrodes in the array. The electrochemistry that is performed involves pulse electrodeposition, whereby the potential of one or more electrodes in the array is reduced to a less positive value than that of one or more precursors in solution to remove one or more electrons from one or more precursors, and then the potential is returned to a more positive value where electrons are not removed from at least one precursor. This pulse is repeated from two to several million times at one electrode until the desired amount of deposit has been formed. The relative concentrations of the precursors in solution are then changed by a small increment to 0.49 mM $CuSO_4$ and 0.51 mM $AgNO_3$ and the pulsed electrochemical process is repeated at a different electrode. This incremental change in relative precursor concentration and subsequent pulsed electrodeposition is repeated until all concentrations of interest have been used to prepare discrete samples on each electrode of the array of 1024 electrodes. Those samples can then be treated using a number of condensed phase and gas phase treatments that include, for example, exposure to carbon monoxide gas. Alternately, those samples can be analyzed for desired activity without treatment. The analysis of those samples can occur by electrochemical interrogation of each sample, of a group of samples, or of all samples using the array of electrodes that supports the samples. This ability to individually address the samples during analysis is an unexpected benefit of preparing the samples onto an array of electrodes. For example, the array of sample-supporting electrodes can be immersed in an 80° C. water solution that contains oversaturated hydrogen gas, and the potential of an individual electrode that support a sample of interest can be held at 0.7 volts positive of the Ag/AgCl redox couple while the current that is passed through the electrode is monitored. That sample-supporting electrode can then be returned to open circuit or another potential, and a similar analysis can be performed at a second sample-supporting electrode. This process can be continued until all of the samples of interest have been examined. The information that is obtained can indicate the array of activities that the array of samples show for oxidizing hydrogen. That array of activities can be examined manually or by algorithmic computer search to indicate samples that show exceptional or unexpected activities for oxidation of hydrogen. Samples which show exceptionally high activities for oxidation of hydrogen can then be employed to indicate compositions of matter that can be useful for devices that are used to oxidize hydrogen, such as fuel cells and electrolytic cells.

EXAMPLE 1

Synthesis and Screening of Anode Catalysts for Fuel Cells

The fabrication and testing of binary phase space at a resolution of one atomic percent (e.g. 100%Pt-0%Ru, 99%

Pt-1%Ru . . . 1%Pt-99%Ru, 100%Ru) requires the fabrication and evaluation of 101 different alloy combinations. The addition of another component increases the number of different ternary compositions to 10,100 and the addition of a fourth component increasing the number to over 1,000,000. The testing and fabrication of such large numbers of materials using traditional methods is unwieldy as to make it experimentally impossible. Consequently, researchers have had to rely on chemical intuition, and scant experimental results, to lead them in the direction of improved catalyst systems. Combinatorial catalyst electrodeposition directly onto an electrode array allows rapid preparation and testing of samples.

Binary compositions can be electrodeposited from aqueous solutions containing metal complexes of the desired metals, in particular $PtCl_4^{2-}$ and $RuCl_6^{3-}$. These dilute solutions have molarities in the range of 1–10 mM. The use of high valence metal anions allows for use of mutually miscible deposition solutions. Suitable experimental conditions for the co-deposition of Pt—Ru compositions on bulk electrochemical electrodes (standard electrodes for electrochemical evaluation) can be initially determined using bulk electrodes. These conditions can then be used for deposition of compositions upon the electrode array.

Overpotential deposition is the method of choice. The fabrication may be automated by computer control of the solution composition in the deposition cell, and, since electrodeposition are carried out at the same overpotentials, morphology variations will be minimized. This similarity in particle size, morphology, and surface area is essential for the comparison of catalytic reactivities of different compositions, simplifying data analysis.

Procedures to be used to electropotentially evaluate the electrocatalysts for methanol and CO oxidation involve two different testing protocols. The reactivity of the electrocatalysts electropotentially in an essentially linear (but extremely rapid and highly automated) fashion is analyzed. The primary method by which the reactivity of the many alloys is examined will be based on direct electrochemical measurement of the electrocatalytic reaction rate. This is done using traditional electrochemical approaches. Previous studies on the activity of Pt—Sn and Pt—Ru alloys toward CO oxidation, used CO stripping voltametry (i.e. predosing the solution with CO, followed by oxidation in a clean electrolyte) may be used as a means of determination of catalytic activity towards CO oxidation. The testing procedure may be modified to measure the current that results from the cathode at specific voltages as the level of carbon monoxide in solution is increased. Test procedures may also evaluate the ability of the catalyst to reactivate itself after exposure to CO.

Evaluation of a 1024 microelectrode array may take place in just over 17 minutes for a given set of conditions. Note that, while these experiments are not strictly combinatorial (i.e., there are no parallel steps in the evaluation, except that same solution conditions are used for each electrode) the development of a highly automated testing instrument achieves the same end goal, namely, the ability to prepare and test extremely large numbers of electrocatalyst compositions in short time periods.

Direct electrochemical potentiometric experiments on the electrode array sequentially and rapidly addresses the individual electrodes with both a potential step and sweep under either hydrostatic or hydrodynamic conditions. The current response of the materials indicates the kinetics for the reactions of interest, e.g. $H_2$ and MeOH oxidation.

The oxidation of MeOH to $CO_2$ on pure platinum occurs at an overpotential 0.5–0.6V above the thermodynamic potential of (+0.043). Consequently, after preparation of an array of materials of varying composition, the array is immersed into a flow cell containing methanol. The entire array of electrodes are biased simultaneously at the overpotential for methanol oxidation (0.7V). The methanol electrooxidation current densities measured will indicate lead compositions worthy of further development and analysis.

EXAMPLE 2

Synthesis and Screening of Cathode Catalysts for Fuel Cells

The combinatorial electrochemistry techniques described above are used to synthesize and characterize known and new catalysts for use as cathode catalysts in fuel cells. The primary desired characteristic in this example is a high rate of reduction of oxygen. A secondary desired characteristic is a high selectivity for oxygen over other species such as methanol.

The aqueous salt solutions used, for example, may include $H_2PtCl_4$ (tetrachloroplatinic acid) and $Cr_2(SO_4)_3$ (chromic sulfate) with $NaNO_3$ electrolyte. Electrodeposition takes place in a typical three electrode configuration comprised of a reference electrode, a counter electrode and the working electrode array. Electrodeposition is carried out under a variety of concentrations, flow rates, currents, potentials, and temperatures to achieve the most smooth and reproducible surfaces. Typically, overpotential deposition, high frequency pulse deposition, and protecting the deposits with passivating layers such as self assembled monolayers, electrooxidizable polymers, and metal oxide coatings allows preparation of smooth, well-controlled samples.

Reduction of $Pt^{2+}$ occurs at ca. −0.2 V and reduction of $Cr^{3+}$ occurs at ca. +0.75 V. Unprotected deposits which include Pt that are allowed to return to open circuit will experience reaction between Pt and $Cr^{3+}$ to give $Pt^{2+}$ (as a dissolved salt) and Cr (as a deposited metal). Thus, the potentials of "inactive" electrodes are controlled to be more positive than +0.75 V.

Rough morphology may be mitigated further by the use of high valence metal anions and the incorporation of complexing agents, such as sulfamate urea or substituted urea derivatives, formamide or other amine additives in the deposition baths. These can increase the polarization of chromium and enhance simultaneous codeposition of both the components of the bath. However, the effects of such additives on the catalysts may interfere with the overall activity of the alloys.

For analysis of the deposited samples, in order to establish a pertinent experimental protocol, catalytic activity can be ascertained first for bulk samples. The primary method of analysis is direct electrochemical measurement of the electrocatalytic reaction rate. This can be done using traditional electrochemical approaches. For instance, CO stripping voltammetry (i.e. pre-dosing the solution with MeOH, followed by oxidation in a clean electrolyte) can be used as a means of determination of catalytic activity towards MeOH activity. This testing procedure is modified to measure the current that results from the cathode at specific voltages as the level of methanol in solution is increased. Test procedures can also be included to evaluate the ability of the catalyst to reactivate itself after exposure to transient MeOH.

Characterization of oxygen reduction catalytic activity can be accomplished via half-cell testing. This method requires the use of an oxygen saturated solution. The compositions are tested at 1.0–0.2 V vs. a reference hydrogen electrode. This test results in the determination of polarization curves for the catalytic oxygen reduction of the various compositions (potential (V) vs. specific current density (A/cm$^2$)).

Resistance to methanol and, by association, carbon monoxide, is measured by introducing methanol in 5 mM increments to the test solution. This step provides an absolute measure of both the selectivity of the catalyst for oxygen reduction and the resistance of the catalyst to methanol or CO poisoning.

EXAMPLE 3

Deposition From Solutions of Metal Precursor Complexes

Deposition from solutions containing the metals as precursor compounds is a flexible aproach, especially with regard to depositing more than one element simultaneously. In the simplest embodiment of this approach, the solution contains a mixture of metal alkoxides. Deposition occurs via an electrochemical process.

For example, if the metals are present as alkoxide precursors and dissolved in a mixed alcohol/water solvent, the deposition could be effected by creating oxidizing conditions at a particular electrode in the array of electrodes. These oxidizing conditions can produce protons, thereby driving the decomposition of the metal alkoxide precursors, precipitating the metal oxide product, and depositing a mixed metal oxide on the electrode. In this simplest case, the deposit comprises a metal oxide with the metal composition being defined by the relative amounts of the metal alkoxide precursors in the original solution.

Control of the metal oxide composition may be achieved by varying the composition of the solution from which the deposition occurs. Thus, this approach is controllable and reproducible to produce varied metal oxide deposits.

Deposition of metals in various host matrices is achieved by addition of the appropriate host compounds. For example, to deposit a metal silicate, a silicon precursor compound such as tetraethoxysilane is added to the solution. Metal aluminates may be deposited from solutions containing aluminum alkoxide reagents, etc.

Several other types of precursors can also be used, including oxalates, acetates, and properly-tuned crown ether complexes. In these cases, dissociation of the complexing agent from the metal center can be driven by redox decomposition of the complex. For the oxalates in particular, this leads to clean production of the "bare" (i.e. solvated) metal ion plus $CO_2$. In the presence of alkoxides such as those discussed above, these metal ions become trapped within the silica or alumina (or other material) matrix. This point is important because it suggests that several different metals can be codeposited from a variety of complexation environments, which will allow for unexpected flexibility in the design of the deposition conditions.

The compositions of typical target phosphors can derive from combinations of the following materials: type A elements (Si, Al, P, B, Mg, Ge, Sn), type B elements (Ba, Sr, Ca, Y, Gd, K, Na), activators (Eu, Tb, Ce), and sensitizers (any other rare earth metal). Host matrices prepared from combinations of the type A and type B elements can then be doped with small amounts (1–15%) of the activators and smaller amounts (0.001–1%) of the sensitizers. Given this method for materials synthesis, an extremely large number of possible phosphors is envisioned. An example is the phosphor defined by Si as the type A elements, a combination of Y and Ba as the type B element, with Ce added as an activator and Nd added as a sensitizer. For this elemental composition, samples are electrochemically prepared that contain the type A element compositionally varied in 5% increments, giving 20 possible combinations. For each of these 20 combinations, the concentration of type B elements in the samples is likewise varied in 5% relative w/w increments, giving a total of about 400 compositions. For each of these, the activator may be varied from 1–15% in 1% increments, giving a total of 6000 compositions. Finally, for each of these, the sensitizer may be varied from 0.001% to 1% in factors of 2 on a logarithmic scale (i.e. 0.001%, 0.003%, 0.01%, etc.) for a total of seven additional variations. This brings the total number of compositions to 42,000 for a fairly simple phosphor material.

For this example, alkoxide complexes for all of the precursor metals can be used. Specifically, these are $Y(OEt)_3$, $Ba(OEt)_2$, $Si(OEt)_4$ and $Eu(OEt)_3$. Deposition is effected in a solution containing 95–99% ethanol and 5–1% $H_2O$. It is necessary to keep the water concentration low, because the presence of large amounts of water in the solution can drive premature hydrolysis of the sol-gel precursors, leading to bulk phase precipitation of the material. In this particular case, sol-gel deposition is achieved by applying a more positive electrode potential. This oxidizes water and leads to hydrolysis of the alkoxide complexes, leading to deposition of a metal silicate containing the metals that were present.

Key variables for the deposition step include: a) the temperature, which influences the rates of the hydrolysis and deposition processes, b) the applied potential, which influences the rate of water oxidation and therefore the rate of generation of protons, c) the manner in which the positive potential is applied, either galvanostatically or potentiostatically, which influences the time dependence of the rate of proton generation, d) the time for the deposition, which influences the amount of material deposited, e) using solution flow to replenish reagents near the electrodes, and f) the structure of the alkoxide or other precursor complex, which affects the stability and hydrolysis rate of the complex. Exploration of these variables may be done at both conventional bulk electrodes and on an array of electrodes.

A fairly wide range of other solution/deposition conditions is envisioned for metal oxide deposition from solution. For example, metal salts can be used in aqueous solutions as precursors for metal-containing thin films of oxides or other phases. In these cases, deposition is driven by interfacial pH changes and/or by changes in the redox state of the metals (i.e. to generate an oxidation state that is not soluble under the solution conditions). This technique may be used to deposit $PbO_2$ films doped with a wide variety of second metals, including As and Bi. Adapting this technique to allow co-deposition of many different, mixed composition metal phases, including oxides, silicates and aluminates, using precursors that are modestly stable in aqueous solutions, at arrays of electrodes is an innovative step.

For example, for aluminates, one can start with solutions containing $NaAlO_2$-like species. Execution of this approach requires identification of suitable precursors and exploration of their regions of mutual stability in aqueous solutions and conditions under which they can be co-deposited.

One more example is of preparation of a simple metal phosphate phosphor. In a typical experimental protocol, the electrode array is housed in a flow cell, so that it can be exposed to a solution of controlled, but variable, composition. For example, for deposition of a europium (II)-doped BaPO$_4$ material a solution containing the appropriate mixture of the rare earth and alkaline earth ions (typically as nitrate salts), plus a source of phosphate (e.g. H$_3$PO$_4$), is introduced into the flow cell. Applying a less postive potential drives water reduction, which causes the pH near the electrode surface to high values. This produces PO$_4^{3-}$ which drives deposition of the target material. This process can be repeated under computer control at many different electrode locations in a given array, but with slight variations in the solution phase composition in order to produce a new and slightly different composition at each electrode. In this way, the entire compositional phase space for the material is examined in a short time.

EXAMPLE 4

Deposition From Colloidal Solutions

An additional approach to deposition of various oxide, silicate, aluminate, and other materials is through the deposition of combinations of small colloidal particles containing the various materials that are desired to be in the deposit. Deposition from colloidal solutions can be achieved by electrochemically driving a flocculation process. In such a case, the material precursors are present as constituents of a colloidal suspension.

Stabilization of such suspensions is typically electrostatic. By control of the surface charge on the particles and the ionic strength of the solution it is possible to generate stable suspensions. Surface charge control is achieved either by manipulating the pH of the solution to take advantage of the acid-base character of the colloidal particles or by manipulating the identity, charge and number of adsorbates on the particles. Ionic strength is used to control the electrostatic repulsion between the particles. Low ionic strength gives greater repulsion and more stability while higher ionic strength gives less repulsion and less stability.

Given this situation, it is clear that deposition from a colloidal suspension can be driven by causing any of several changes in the solution conditions near the electrodes in the array of electrodes. For example, a simple case involves the use of colloidal particles that are stabilized by surface charges that derive from acid-base chemistry at the particle surface. An example is $\gamma$-Al$_2$O$_3$. This material has a pH$_{pzc}$ of 8.5. Thus, at pH values below 8.5, the net surface charge is positive. Application of reducing potentials at an electrode in an aqueous solution containing such particles drives water reduction. This leads to an increase in the pH near the electrode. If this pH change is carefully controlled, conditions can be created near the surface that cause the particle surface charges to approach zero. This leads to instability of the colloidal suspension and results in deposition of the particles.

More complicated scenarios are needed to describe the deposition of more than one element using this approach. In these cases, solutions containing more than one stable colloidal suspension are prepared. For example, stable suspensions of metal oxides and silicates can be prepared. Again, adequate stability can be achieved by using suitable solutions and ionic strengths so that all the particles in solution bear a net positive (or negative) charge and experience significant electrostatic repulsion due to low ionic strength. Appropriate control of solution conditions enable colloid mixtures to be compatible (with respect to flocculation).

An issue in this approach is how the activators and sensitizers can be incorporated into the deposits. New synthetic procedures allow oxidative decomposition of precursor complexes of the activators and sensitizers during deposition of the colloidal particles.

As will be understood by ordinary skill in the art, the present invention may be embodied in other forms without departing from the essentials thereof Accordingly, disclosure of the preferred embodiment is intended to be illustrative, but not limiting, of the scope of the invention which is set forth in the following claims.

What is claimed is:

1. An apparatus for rapidly applying at least one component of each of at least two materials to addressable predefined locations on an array of electrodes, the apparatus comprising:
  at least two electrodes contained in said array; and
  an assembly for applying an electrical potential or current from a power source to each of the electrodes, wherein the electrodes are addressable through the assembly, and wherein said at least one component of said each of said materials is operatively supplied to the array of electrodes, said electrical potential or current causing the components of the materials to deposit at said addressable predefined locations and wherein said at least one component of each of the at least two materials deposited on the at least one second electrode varies in composition from the at least one component of each of the at least two materials deposited on the at least one first electrode, whereby the depositing of said components lead to controllable morphologies at each said at least one electrode.

2. The apparatus of claim 1, wherein said electrodes are the addressable predefined locations.

3. The apparatus of claim 2, wherein the assembly includes a controller to control the electrical potential or current for each said electrode.

4. The apparatus of claim 3, wherein the electrode array includes at least twenty said electrodes.

5. The apparatus of claim 4, wherein the electrode array includes at least one hundred said electrodes.

6. The apparatus of claim 5, wherein the electrode array includes at least ten thousand said electrodes.

7. The apparatus of claim 5, wherein said assembly includes a reference electrode.

8. The apparatus of claim 7, wherein the reference electrode is movable to operatively adjust depositions.

9. The apparatus of claim 5, wherein said assembly includes a counter electrode.

10. The apparatus of claim 9, wherein the counter electrode is movable to operatively adjust depositions.

11. The apparatus of claim 5, wherein the array of electrodes includes a highly resistive substrate below said electrodes, a highly conductive material above said highly resistive substrate and around said electrodes, and a second highly resistive material above said highly conductive material and around said electrodes wherein the second highly resistive material does not cover the electrodes.

12. The apparatus of claim 11, wherein the array of electrodes is a microelectrode array.

13. The apparatus of claim 12, wherein the electrodes are at most 1 mm in diameter.

14. The apparatus of claim 13, wherein the electrodes are at most 100 $\mu$m in diameter.

15. The apparatus of claim 5, wherein said at least one component of said each of at least two materials is entrained in a solution when operatively supplied to said assembly.

16. The apparatus of claim 15, wherein at least one of said at least one component is a kinetically sluggish precursor.

17. The apparatus of claim 15, wherein said solution includes at least two passivating agents.

18. The apparatus of claim 5, wherein the assembly includes a flow cell, whereby the at least one component of said each of the at least two materials is supplied to the array of said electrodes in varying concentrations of said components.

19. A method of rapidly applying at least one component of each of at least two materials to addressable predefined locations on an array of electrodes, comprising:

applying a potential to at least one first electrode on said array of electrodes;

depositing at least said at least one component of each of the at least two materials onto said at least one first electrode;

applying a second potential to at least one second electrode on said array of electrodes;

depositing at least said at least one component of each of the at least two materials onto said at least one second electrode, wherein said at least one component of each of the at least two materials deposited on the at least one second electrode varies in composition from the at least one component of each of the at least two materials deposited on the at least one first electrode whereby the depositing of said components lead to controllable morphologies at each said at least one electrode.

20. A method of rapidly applying at least one respective component of each of at least two materials to addressable predefined locations on an array of electrodes, comprising:

varying concentrations of the components over time;

applying a potential to at least one first electrode on said array of electrodes;

depositing at least the components onto said at least one first electrode to form a respective deposit on each of said at least one first electrode;

applying a second potential to at least one second electrode on said array of electrodes;

depositing at least said components onto said at least one second electrode to form a respective deposit on each of said at least one second electrode, wherein said components deposited on the at least one second electrode vary in composition from the components deposited on the at least one first electrode whereby the depositing of said components lead to controllable morphologies at each said at least one electrode.

21. The method of claim 20, wherein said components are supplied by a flow cell.

22. The method of claim 21, wherein said applying steps include adjusting the potential to operatively supply an overpotential at said at least one electrode whereby the depositing of said components leads to uniform morphologies at each said at least one electrode.

23. The method of claim 21, wherein said applying steps include controlling the potential at each said at least one electrode by pulse electrodeposition whereby a depositing potential is applied followed by a resting potential in cycles until said each at least one electrode is deposited with said respective composition.

24. The method of claim 21, wherein said applying steps include applying a second potential to the other electrodes in the array whereby the electrodes not being supplied a depositing potential are supplied a holding potential to prevent exchange reactions.

25. The method of claim 21, wherein said components are kinetically sluggish precursors.

26. The method of claim 21, wherein said varying step includes moving a reference or counter electrode.

27. The method of claim 21, wherein said applying step and said depositing step is repeated one thousand times in rapid sequence whereby at least one thousand different compositions are deposited onto the array of electrodes.

28. The method of claim 20, wherein said depositing steps include controlling the morphology of each of said deposits.

* * * * *